(12) United States Patent
Calloch et al.

(10) Patent No.: US 7,017,423 B2
(45) Date of Patent: Mar. 28, 2006

(54) METHOD, DEVICE AND MACHINE FOR PURE BENDING TEST OPTIONALLY ALTERNATING

(75) Inventors: Sylvain Calloch, Antony (FR); David Dureisseix, Cachan (FR); Gilles Arnold, Bagneux (FR); Inaki Zudaire Rovira, Molins de Rei (ES)

(73) Assignee: Centre National de la Recherche Scientifique (CNRS), (FR)

( * ) Notice: Subject to any disclaimer, the term of this patent is extended or adjusted under 35 U.S.C. 154(b) by 0 days.

(21) Appl. No.: 10/524,474

(22) PCT Filed: Aug. 12, 2003

(86) PCT No.: PCT/FR03/02515

§ 371 (c)(1),
(2), (4) Date: Feb. 11, 2005

(87) PCT Pub. No.: WO2004/017047

PCT Pub. Date: Feb. 26, 2004

(65) Prior Publication Data

US 2005/0241405 A1   Nov. 3, 2005

(30) Foreign Application Priority Data

Aug. 13, 2002  (FR)  .................................. 02 10261

(51) Int. Cl.
G01N 3/20     (2006.01)

(52) U.S. Cl. ....................................................... 73/849

(58) Field of Classification Search ..................... None
See application file for complete search history.

(56) References Cited

U.S. PATENT DOCUMENTS

| 3,786,673 A | 1/1974 | Weissmann |
| 3,952,572 A * | 4/1976 | Mergler et al. ............... 72/298 |
| 5,284,058 A * | 2/1994 | Jones .......................... 73/579 |

FOREIGN PATENT DOCUMENTS

| DE | 197 29 438 A | 2/1999 |
| FR | 2 247 139 A | 5/1975 |
| GB | 627 501 A | 8/1949 |
| SU | 714 221 A | 2/1980 |

OTHER PUBLICATIONS

Brunet et al: "Nonlinear Kinematic Hardening . . . ", Journal of Engineering Materials, vol. 123, No. 4, Oct. 2001, pp. 378-383.

(Continued)

*Primary Examiner*—Max Noori
*Assistant Examiner*—Octavia Davis
(74) *Attorney, Agent, or Firm*—Lerner, David, Littenberg, Krumholz & Mentlik, LLP

(57) ABSTRACT

The present invention provides a method, apparatus, and a machine for testing in pure bending, optionally in alternating bending. Two mutually identical testpieces are subjected to optionally alternating opposing bending movements while conserving mutual symmetry about a point, under drive from two controlled motor assemblies that are free to move relative to each other. Interfering forces induced in the two testpieces during testing are minimized, and the performance of the testpieces in pure bending can be studied with increased accuracy.

33 Claims, 10 Drawing Sheets

OTHER PUBLICATIONS

Yoshida et al. "Identification of Materials . . . ", INT. Journal of Mech. Sci., vol. 40, No. 2-3, 1998, pp. 237-249.

S. Calloch et al, "A Pure Bending Machine to Identify the Mechanical Behaviour of thin sheets", 6th International Esaform Conference on Material Forming, Apr. 28-30, 2003.

* cited by examiner

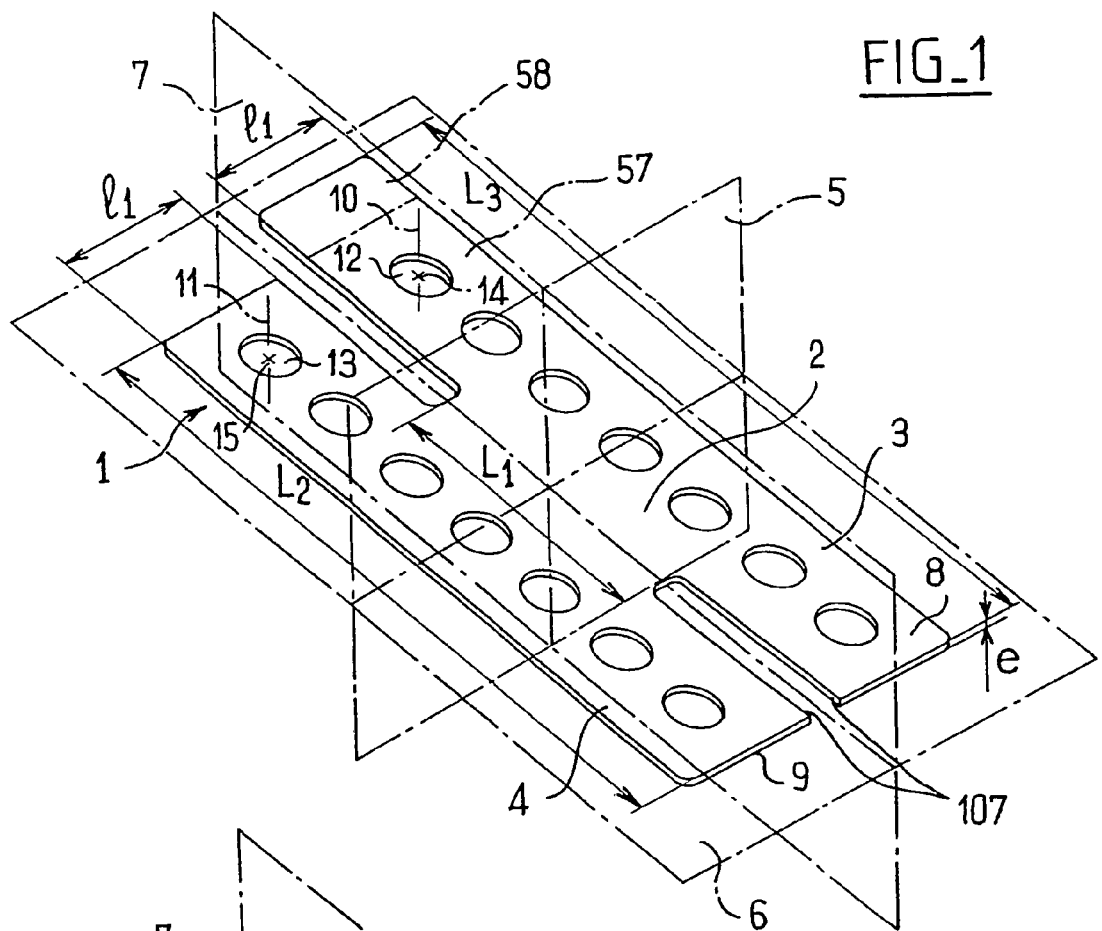
FIG_1
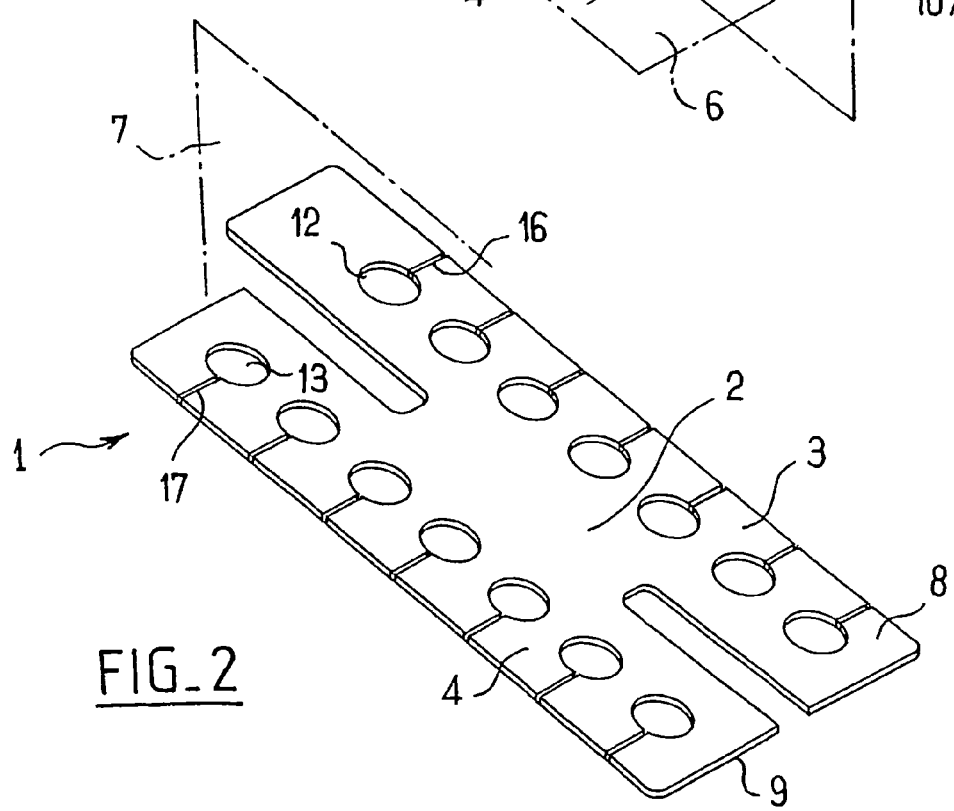
FIG_2

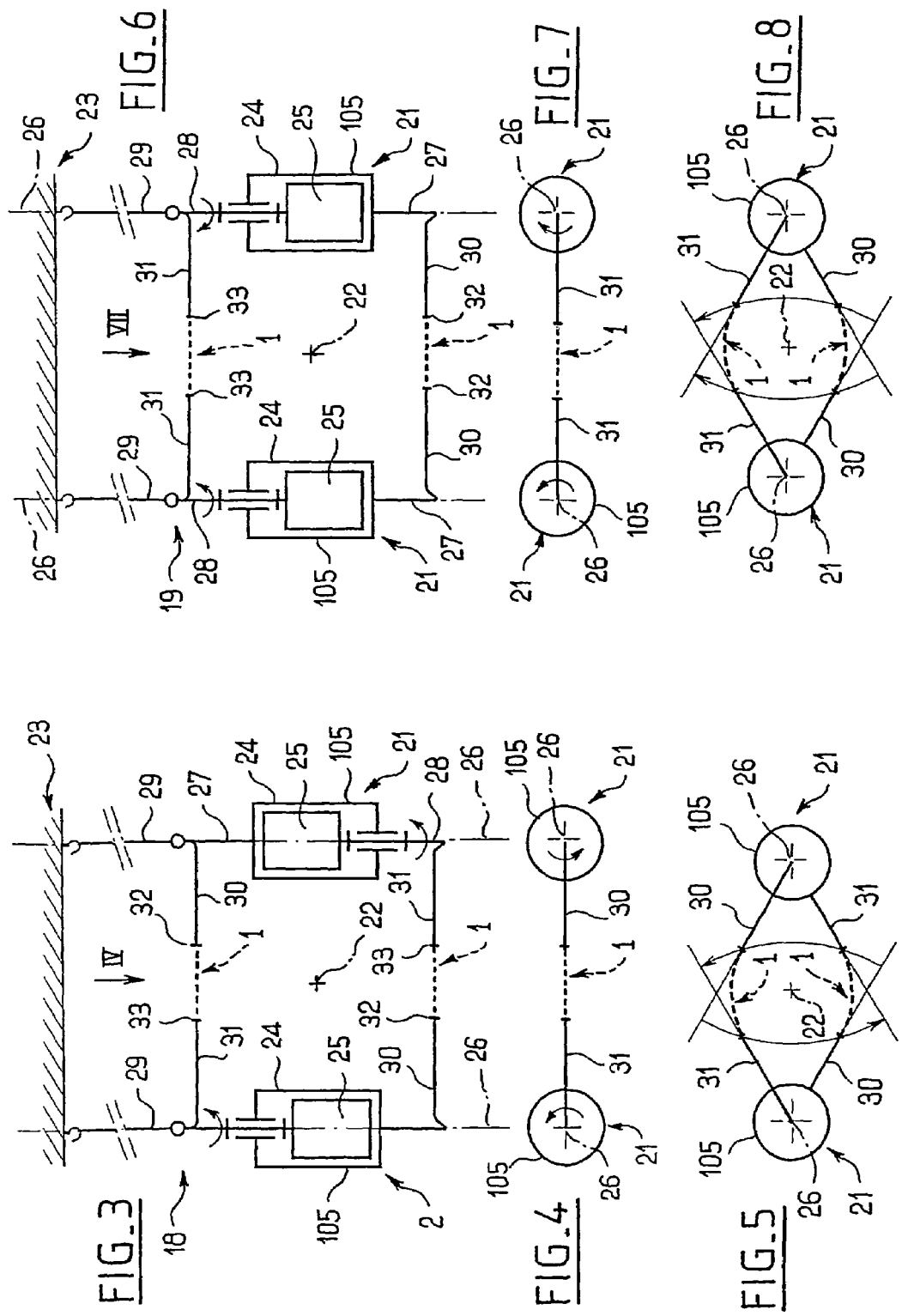

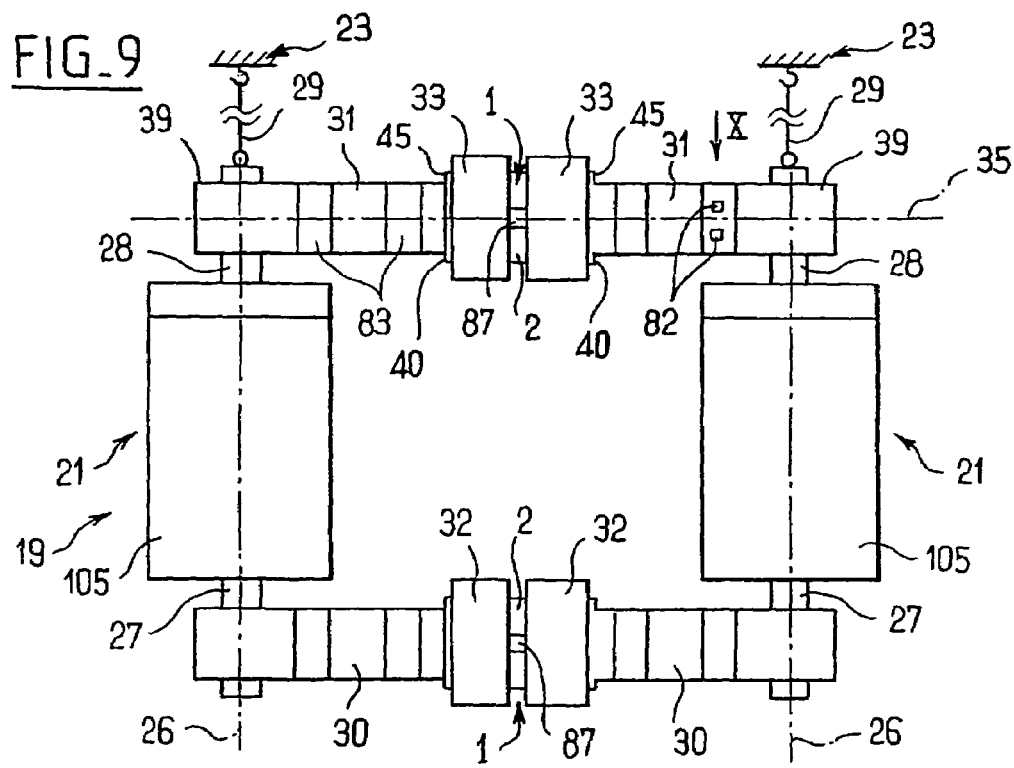
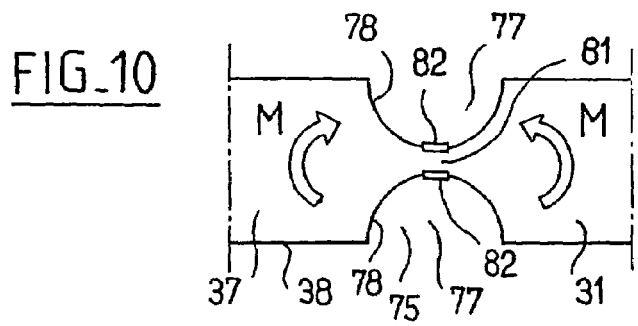
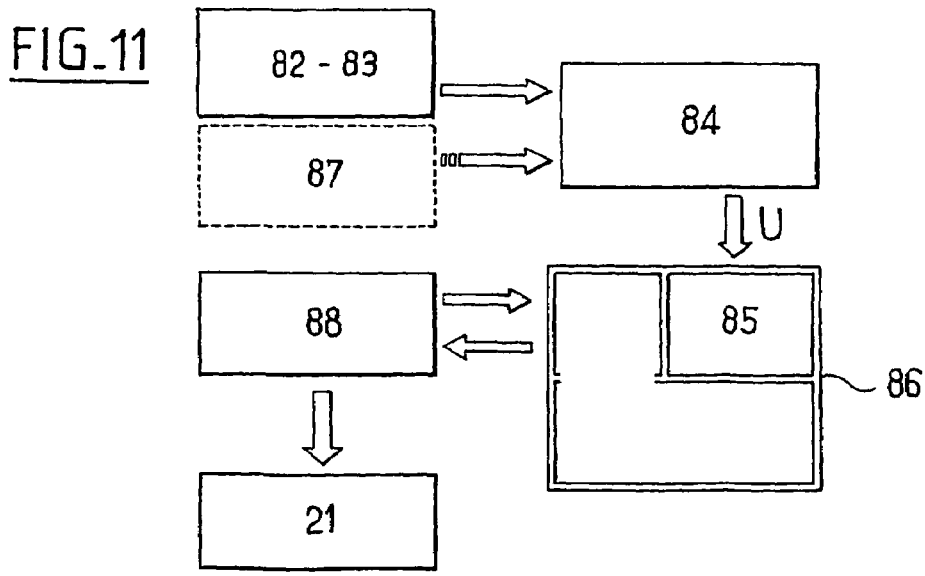

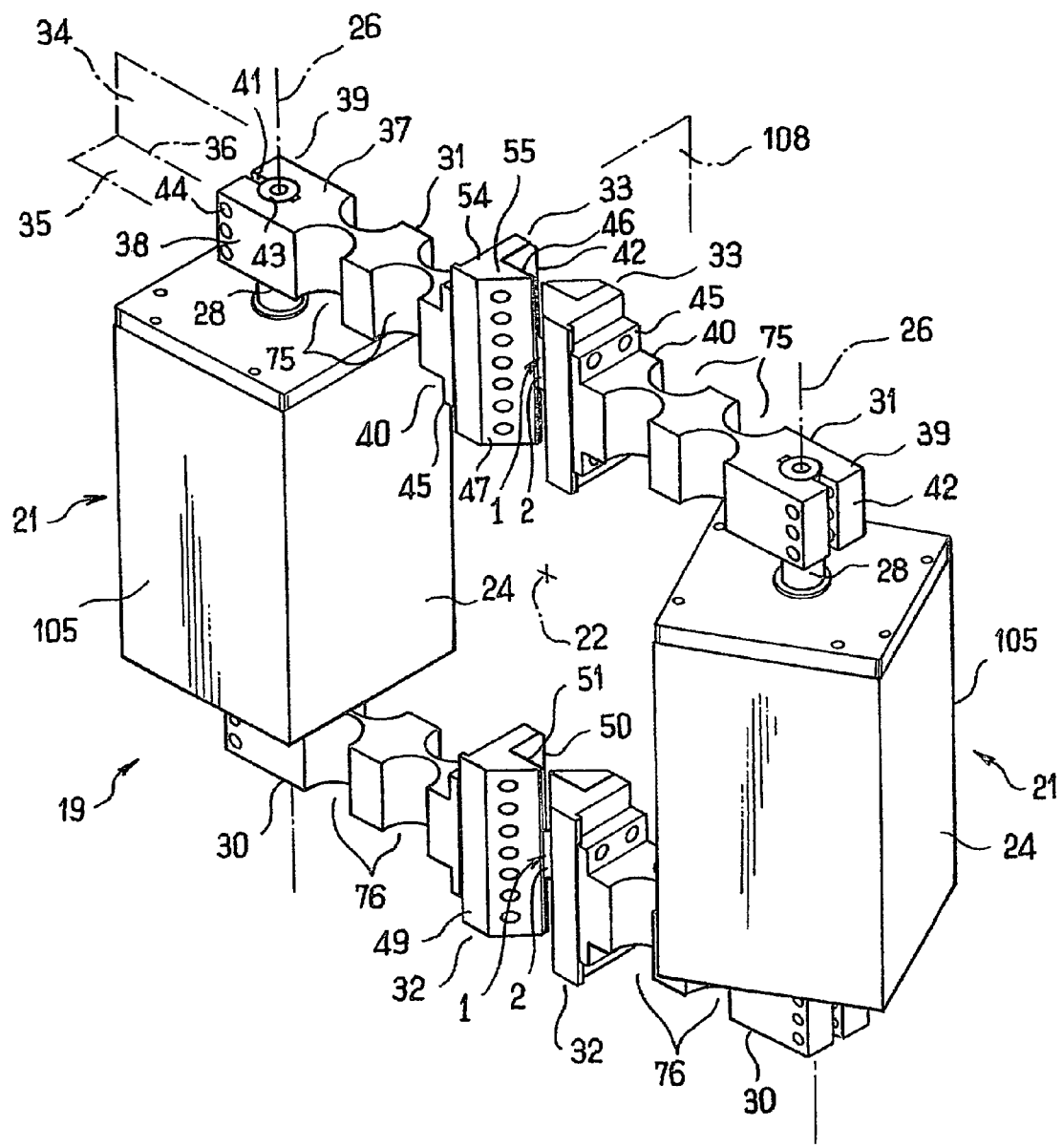
FIG_12

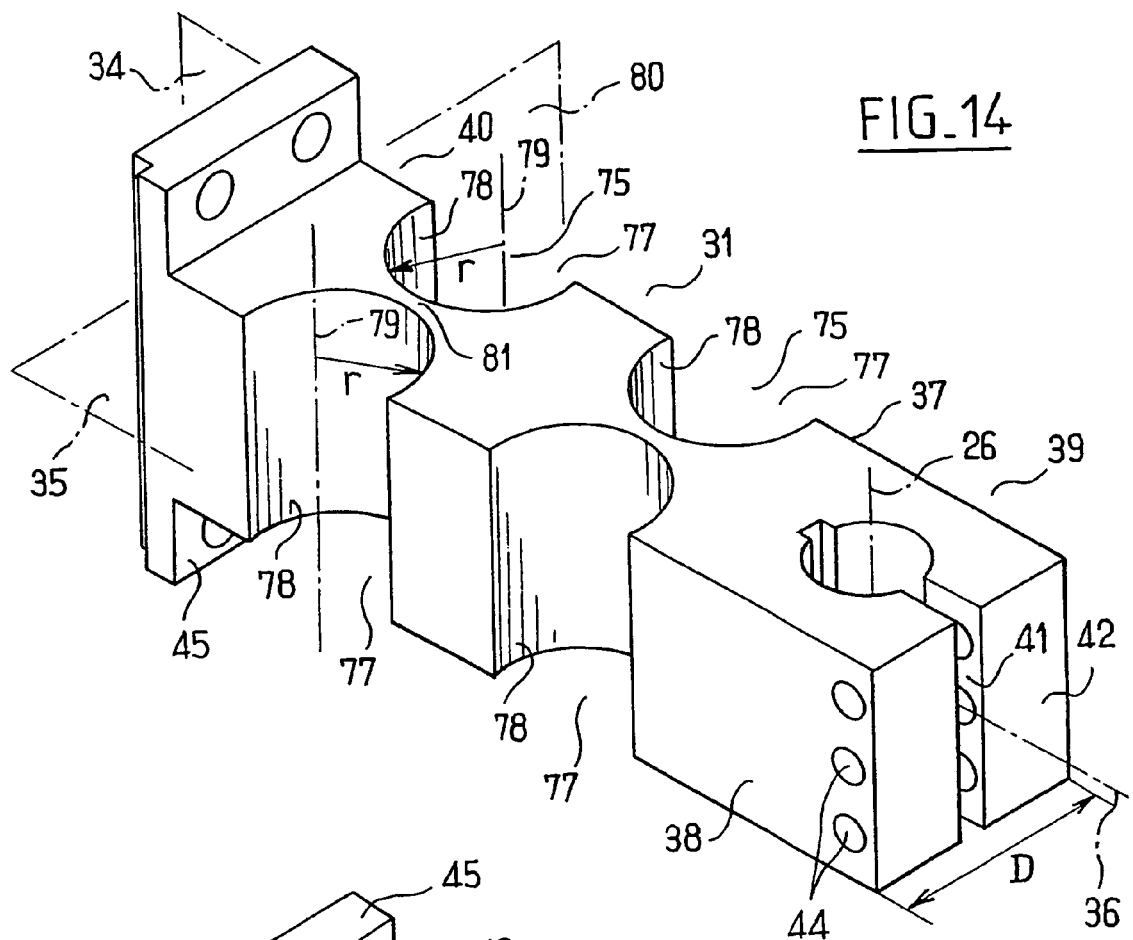
FIG_14
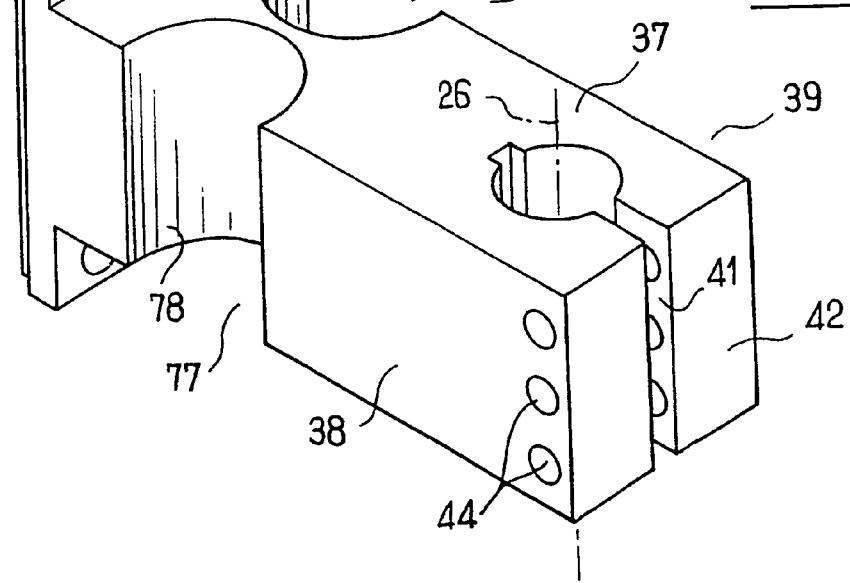
FIG_15

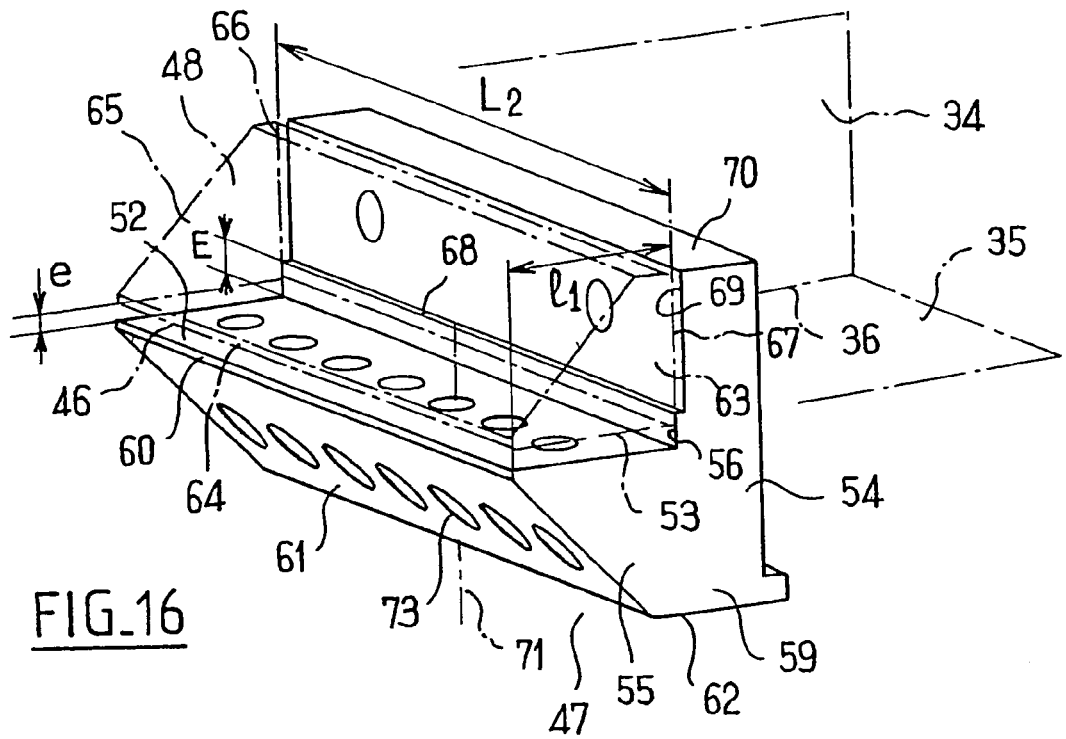
FIG_16
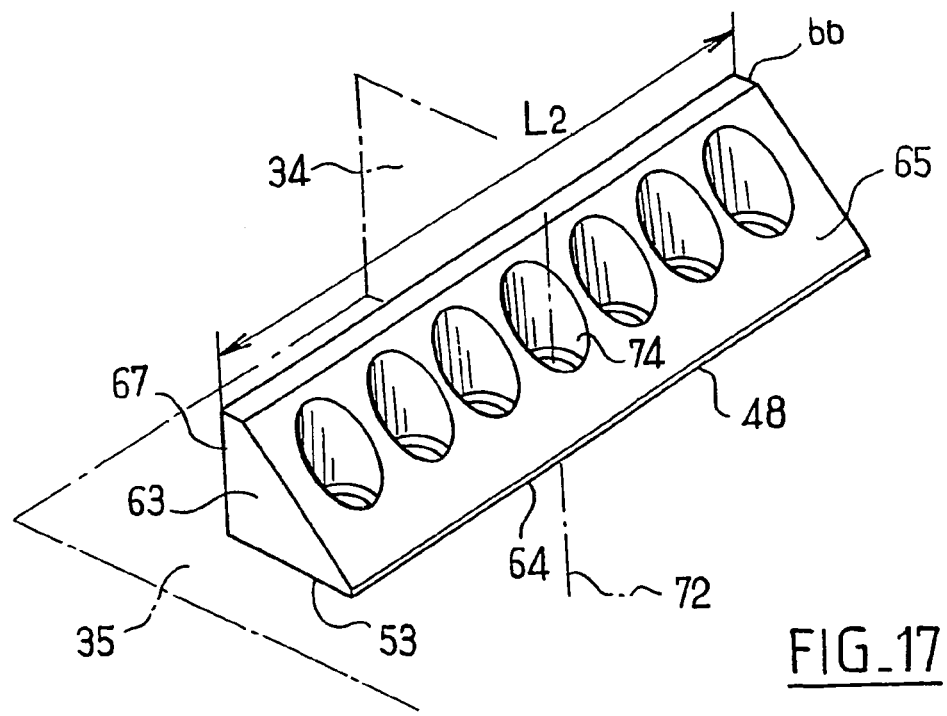
FIG_17

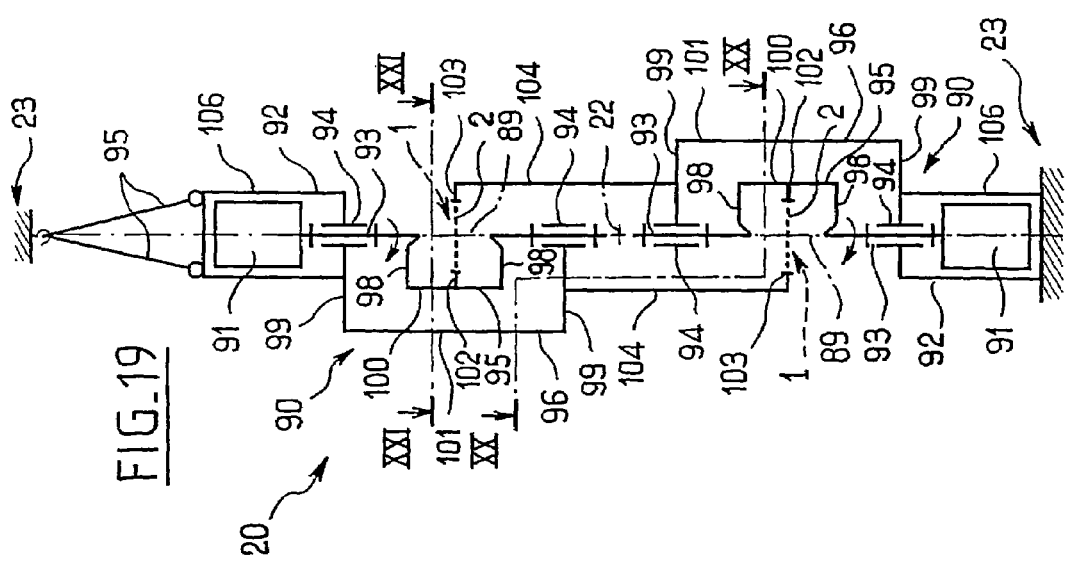

METHOD, DEVICE AND MACHINE FOR PURE BENDING TEST OPTIONALLY ALTERNATING

CROSS REFERENCE TO RELATED APPLICATIONS

The present application is a national phase entry under 35 U.S.C. § 371 of International Application No. PCT/FR03/02515 filed Aug. 12, 2003, published in France, which claims priority from French Application No. 02/10261 filed Aug. 31, 2002, all of which are incorporated herein by reference.

This application is a 371 of PCT/FR03/02515.

The present invention relates to a method of testing in pure bending, optionally in alternating bending, the method comprising the following succession of steps:

a) making or selecting a testpiece having two mutually opposite end grip zones and a bending zone interconnecting the two grip zones, said testpiece presenting, in a rest state, a first mean plane crossing the bending zone and each of the grip zones and constituting a first plane of symmetry at least for the bending zone, and a mean surface for the bending zone and each of the grip zones, which mean surface is perpendicular to the first mean plane;

b) while leaving the testpiece in the rest state, rigidly securing its two grip zones so as to define for each of them a respective pivot axis perpendicular to the first mean plane and occupying a determined position firstly relative to the respective grip zone and secondly relative to the mean surface; and c) imparting controlled opposing turning movements to the two grip zones of the testpiece, optionally in alternation, about the respective pivot axes and away from the rest state, while leaving the pivot axes free to move towards each other or apart from each other, so as to impart optionally alternating bending to the bending zone and so as to study the behavior of the bending zone in pure bending, for example by measuring the resistance opposed to said turning movement by at least one of the grip zones of the testpiece in order to deduce therefrom how the resistance to pure bending of the bending zone changes.

BACKGROUND OF THE INVENTION

By convention, it is considered that a bending test in pure bending is a bending test that is implemented while inducing as little parasitic force as possible into the bending zone of the testpiece, i.e. more specifically as little normal and/or intersecting force as possible.

In the context of the present application, when it is said that the turning movement is optionally alternating, or that a test in pure-bending is optionally in alternating bending, that constitutes a convenient shorthand for specifying in particular that:

the changes in turning during a test may be monotonic, i.e. always in the same direction, or with one or more reversals of direction; and if there is a reversal of direction, the maximum amplitudes in opposite directions may be equal or different.

Such a method is described in an application to performing alternating pure bending tests by M. Brunet, F. Morestin, and S. Godereaux (2001, "Non-linear kinematic hardening identification for anistropic sheet metals with bending-unbending tests", Journal of Engineering Materials and Technology, Vol. 123, pp. 378–383), who also describe apparatus and a machine for implementing the method.

That known method is applied to a single testpiece, as do all previously-known methods of alternating bending testing. Nevertheless, in a manner specific to that method, each of the grip zones of the testpiece is held securely in a respective clamp mounted to pivot about a respective axis in a respective slider and engaged with a common device for driving both clamps and suitable for imparting thereto, and also to the grip zones of the testpiece to which they are respectively secured, alternating opposite turning movements about the respective pivot axes relative to the respective sliders so as to impart alternating bending to the bending zone of the testpiece between the clamps. The pivot axes of the two clamps are mutually parallel and the two sliders are mounted to slide on a common slideway in a direction perpendicular to the two pivot axes, thus allowing the axes to move towards each other or apart from each other along said direction as a function of variation in the apparent length of the testpiece between the two grip zones, i.e. between the two clamps, depending on the bending state of its bending zone.

The pivotal mounting of each clamp about the respective pivot axis in the respective slide takes place via a respective shaft, which shaft is secured to each clamp to lie on the corresponding pivot axis, and is engaged in two bearings of the corresponding slide. Between these two bearings, the shaft meshes via a respective gear train with a respective drive shaft, itself mounted to turn in two bearings of the corresponding slide about an axis that is parallel to the respective pivot axis and that is disposed relative thereto in such a manner that the axes of rotation of the drive shafts corresponding to the two slides, i.e. corresponding to the two clamps, are further apart from each other than are the pivot axes of the clamps. Each drive shafts itself acts via an Oldham joint disposed opposite from the corresponding clamp relative to the corresponding slide, to engage a respective outlet shaft of the drive device which is constituted by an electric motor associated with a torque limiter.

The bending zone of the testpiece can thus be subjected to bending alternately in one direction and in the other, through an amplitude that is adjusted by adjusting the magnitude of the turning of each clamp about the corresponding pivot axis relative to the corresponding slide, said magnitude of turning being identical at all times for both clamps because they are driven in common.

In that known apparatus, the resistance opposed by the clamps and by the grip zones of the testpiece against alternating turning is measured by sensors disposed on the drive shafts between the Oldham joints and the slides, in order to measure the twisting stresses of the drive shafts, where changes in such resistance serve to deduce changes in the resistance to bending of the bending zone.

That prior art apparatus makes it possible continuously to control the pivoting of each grip zone about its pivot axis, i.e. the bending of the bending zone between the grip zones, thereby constituting a significant advance over earlier apparatuses, in particular over the apparatus which appears previously to have been the most satisfactory in terms of maximum bending amplitude, in particular on a testpiece of small thickness, as measured perpendicularly to its mean surface, i.e. the apparatus described by F. Yoshida, M. Urabe, and V. V. Toropov (1998, "Identification of material parameters in constitutive model for sheet metals from cyclic bending test", International Journal for Mechanical Sciences, Vol. 40, pp. 237–249).

The apparatus described by Yoshida et al. acts positively by means of a drive motor in alternating turning only on a first one of the grip zones of the testpiece, while the second grip zone is merely held at a determined orientation relative to a frame that also carries the motor by means of slideway-and-slider assemblies allowing it to move along two mutually perpendicular directions in order to allow the first grip zone to change its direction and in order to accommodate variations in the apparent length of the bending zone between the two grip zones while alternating bending is being applied.

In the apparatus of Yoshida et al., the bending zone thus serves as means for transmitting movement from the grip zone that is directly connected to the motor for drive in alternating turning motion to both the other grip zones, and also the slider-slideway assemblies that serve to maintain a constant orientation, and as a result the non-negligible friction that appears in the connections between the sliders and the slideways leads to non-negligible interfering forces appearing in the testpiece and more precisely in its bending zone, so bending conditions remain remote from ideal conditions of pure bending. This leads to a non-negligible amount of error in determining the changing resistance to bending of the bending zone from a measurement of the resistance opposed to the alternating turning movements by the grip zone that is connected to the motor.

Simultaneous positive action in pivoting on both grip zones of the testpiece enables the two grip zones to be guided in a single direction only, i.e. in practice it enables the two clamps to be guided to slide relative to each other in a single direction only in the apparatus of Brunet et al., thereby enabling friction to be reduced in comparison with the apparatus of Yoshida et al., and consequently reducing the parasitic forces induced in the bending zone by the friction and the disturbances that follow therefrom when studying changes in the bending resistance of the bending zone, with the study thus being less remote from pure bending, but with the friction and the parasitic forces still remaining perceptible. In other words, the twisting stresses measured on the drive shafts of the apparatus of Brunet et al. are due not only to the bending resistance of the bending zone, but also to the resistance due to friction that the slides encounter against the slideway whenever they need to move towards each other or apart from each other as a function of variations in the apparent length of the bending zone between the grip zones, i.e. between the clamps; in addition, the twisting stresses are also associated in part with the resistance opposed to turning by the shafts carrying the clamps in their bearings in the slides, by the gearing transmitting motion between these shafts and the drive shafts, and by the drive shafts in their own bearings in the slides, and that too can lead to a non-negligible amount of error in interpreting these twisting stresses in terms of the bending resistance of the bending zone.

SUMMARY OF THE INVENTION

The object of the present invention is to remedy at least some of the drawbacks of the method and apparatus described by Brunet et al., and in preferred implementations of the present invention, to remedy all of those drawbacks.

To this end, the present invention provides a method of testing in pure bending, optionally in alternating bending, the method comprising the following succession of steps:

a) making or selecting a testpiece having two mutually opposite end grip zones and a bending zone interconnecting the two grip zones, said testpiece presenting, in a rest state, a first mean plane crossing the bending zone and each of the grip zones and constituting a first plane of symmetry at least for the bending zone, and a mean surface for the bending zone and each of the grip zones, which mean surface is perpendicular to the first mean plane;

b) while leaving the testpiece in the rest state, rigidly securing its two grip zones so as to define for each of them a respective pivot axis perpendicular to the first mean plane and occupying a determined position firstly relative to the respective grip zone and secondly relative to the mean surface; and c) imparting controlled opposing turning movements to the two grip zones of the testpiece, optionally in alternation, about the respective pivot axes and away from the rest state, while leaving the pivot axes free to move towards each other or apart from each other, so as to impart optionally alternating bending to the bending zone and so as to study the behavior of the bending zone in pure bending, for example by measuring the resistance opposed to said turning movement by at least one of the grip zones of the testpiece in order to deduce therefrom how the resistance to pure bending of the bending zone changes, as described by Brunet et al., this method being characterized, according to the present invention, in that it is applied simultaneously to two mutually identical testpieces by implementing:

step b) in such a manner that the first mean planes of the two testpieces are mutually parallel and the mean surfaces of the two testpieces are mutually symmetrical about a point when the two testpieces are in the rest state, and in such a manner that the pivot axes of the two testpieces are common and mutually symmetrical about said point; and step c) by applying optionally alternating opposing torques in controlled manner about each pivot axis to the respective corresponding grip zones so as to impose optionally alternating opposing bending movements to the bending zones of the two testpieces, while allowing the pivot axes to move freely relative to each other.

Under such conditions, it is each testpiece which acts via its grip zones interconnected by the bending zone and opposes bending resistance to the bending zone of the other testpiece between its grip zones, without it being necessary to provide any kind of guidance for the grip zones relative to any kind of structure, and consequently avoiding any risk of inducing parasitic forces due to friction into the bending zone of either testpiece. Thus, the measurement of the resistance opposed to turning by at least one of the grip zones is much more representative of the resistance opposed by the bending zone in pure bending, it being understood that by having identical testpieces with the optionally alternating pure bending test being performed simultaneously on both of them makes it possible to conserve symmetry permanently, at least to within a good approximation, between the two testpieces in the state when they are bent in opposite directions and also when in the rest state, said symmetry being about the point or center of symmetry, i.e. both testpieces have their bending zones subjected to the same bending state, if any, and consequently the bending zones of the two testpieces oppose substantially identical resistance to pure bending.

In association with the characteristics of the method of the invention and with the advantageous consequences to which they give rise in this way, the present invention also provides apparatus for testing a testpiece of the type described in the introduction, the testing being in pure bending, optionally in alternating bending, and the apparatus comprising:

a pair of clamps each defining a slot for securely gripping a respective grip zone of the testpiece, the slots presenting, in a relative rest position corresponding to the testpiece being in the rest state, a first mean plane which crosses each of the slots, and a mean surface for each of the slots, with each slot presenting on either side of the mean surface a respective clamping face for clamping the corresponding grip zone of the testpiece and with the mean surface extending perpendicularly to the first mean plane of the slots;

means for defining a respective pivot axis for each clamp in such a manner that in the relative rest position of the clamps, the pivot axes are perpendicular to the first mean planes of the slots, and occupy determined positions relative to the corresponding clamps and are free to move towards each other or apart from each other;

controlled means for imparting opposing, optionally alternating turning movements to the clamps about the corresponding pivot axes away from the relative rest position of the clamps, while leaving the pivot axes free to move towards each other or apart from each other; and means for measuring the behavior of the bending zone of the testpiece in pure bending, e.g. comprising:

means for measuring the resistance opposed to said turning movement by at least one of the clamps, and where appropriate;

means for deducing therefrom the changes in the bending resistance of the testpiece between the clamps, as proposed by Brunet et al., said apparatus being characterized in that, in order to implement the method of the invention, it includes two mutually identical sets of said pair of clamps, having the first mean planes of their slots mutually parallel and having the mean surfaces of the slots mutually symmetrical about a point when the two sets are occupying their rest positions in which each of them is suitable for receiving a respective testpiece in the rest position with the two testpieces being in a relative position such that they are mutually symmetrical about said point;

the means for defining the pivot axes of the clamps of the two sets are arranged in such a manner that the pivot axes are common to both sets, being mutually symmetrical about said point when the two sets are occupying their rest positions, and being free to move relative to each other; and the controlled means for imposing opposing and optionally alternating turning movements on the clamps of the two sets comprise controlled motor means for applying opposing, optionally alternating torques about each pivot axis to the corresponding clamps.

In the meaning of the present invention, mutual symmetry of the mean surfaces of the slots about the point or center of symmetry includes the special case in which said mean surfaces are plane and coincide in a plane that includes the point or center of symmetry.

In the apparatus, the two testpieces constitute the only mechanical connections between two mutually identical motor assemblies, each of which comprises:

two clamps, each of which is suitable for securely receiving a respective grip zone of a corresponding testpiece;

means for defining a relative pivot axis for the two clamps and occupying a determined position relative to each of the two clamps while in a relative rest position; and controlled motor means for imparting relative and optionally alternating turning movements to the clamps about the relative pivot axis away from the relative rest position, and these two motor assemblies, together with control means for the motor means of the two motor assemblies serving to impose relative turning movement, optionally in alternation, on the respective clamps about the respective relative pivot axes, and possibly also together with means for measuring the resistance opposed to the relative turning movement by at least one of said clamps, constitute a machine for testing in pure bending, possibly in alternation, itself characteristic of the present invention and for implementing the method of the invention.

Naturally, it is necessary to carry or support the apparatus of the invention constituted by the machine as designed in this way together with the two testpieces, by carrying or supporting each of said mutually identical motor assemblies, however it is possible for this purpose to use means that induce interfering forces in the two testpieces that are much smaller and much less harmful than those induced by friction between slides and slideways in the prior art apparatuses described above, and thus leading to much less disturbance of the pure bending state in the bending zones and thus to much less disturbance in the study of changes in the bending resistance opposed by the bending zones on the basis of measuring the resistance opposed by at least one of said clamps to being turned.

By way of example, it is possible for this purpose to use an air cushion or a hydraulic mat on which the entire apparatus is allowed to rest freely, or the motor assemblies of the machine can be suspended via flexible ties from a point that is situated as high as possible above the machine, or one of the motor assemblies can be rigidly supported by a rigid support while the other one is suspended in the above-specified manner so that its weight is not transmitted to the first motor assembly via the two testpieces, where these examples are not limiting in any way.

It should be observed that the method, the apparatus, and the machine of the invention may be used with testpieces presenting a variety of shapes in the rest state, and in particular:

any shape of constant section, perpendicularly to the first mean plane and to the mean surface, in particular in the bending zone;

shapes that are curved or plane for their mean surfaces which when plane, may optionally constitute a second plane of symmetry, at least for the bending zone;

or indeed shapes that are optionally symmetrical, at least for the bending zone, about a third mean plane that is perpendicular to the first mean plane and crossed by the bending zone, with the grip zones being disposed respectively on either side thereof, these examples not being limiting.

Thus, as non-limiting examples, two mutually identical testpieces may be subjected to a bending method of the invention, optionally an alternating bending method, each of which testpieces is in the form of a plate of constant thickness as measured perpendicularly to its mean surface, and each of which is flat, in particular in its bending zone, as can be the case for a sample of raw sheet metal, or else it can be curved or corrugated, in particular in its bending zone, as can be the case for a sample of the wall of a metal receptacle or of sheet metal unwound from a coil, or a sample of wall for a metal bellows, or indeed a testpiece in the form of a rod that is curved or rectilinear, of section that is constant, at least in its bending zone, or indeed a testpiece in the form of a plate or a rod in which the bending zone tapers from one of the grip zones to the other.

In contrast, it would appear that the method described by Brunet et al., given the way in which the two clamps are driven to pivot about their pivot axes and the way in which the slides are guided in a direction perpendicular to said axes, is capable of being applied only to testpieces that present in the rest state, and that conserve in the bent state, at least two mutually perpendicular planes of symmetry, one of which is the above-mentioned first plane of symmetry and the other of which is the above-mentioned third plane of symmetry oriented perpendicularly to the sliding direction of the two slides and permanently constituting a plane of symmetry between the clamps in the apparatus of Brunet et al.

In this respect, in the context of the present application, the terms "first", "second", and "third" planes of symmetry are used for convenience of language, and in particular:

mention of a first plane of symmetry does not necessarily imply that there are any other planes of symmetry; and mention of a third plane of symmetry does not necessarily imply that there is a second plane of symmetry.

If, as is often the case, the testpiece in its rest state presents a mean surface constituting a second mean plane that constitutes a second plane of symmetry at least for its bending zone, as applies for example to a testpiece in the form of a rectilinear rod or a testpiece in the form of flat plate, then:

step b) is implemented-in such a manner that the second mean planes of the two testpieces coincide when the two testpieces are in the rest state and the pivot axes are placed in the second mean planes, which thus coincide; and in the apparatus-of the invention, if the slots of each pair of clamps present as their mean surfaces respective second mean planes of symmetry between the clamping faces of each clamp, when in a rest position, then the machine is arranged in such a manner that the second mean planes of the two sets of said pair of clamps are mutually symmetrical about the point or center of symmetry when the two sets are in the rest position, said mutual symmetry including the special case in which said second mean planes of the two sets of pairs of clamps coincide and include the point or center of symmetry.

Similarly, if the testpiece in its rest state presents a third mean plane that is perpendicular to the first mean plane, is crossed by the bending zone when the grip zones are disposed respectively on either side thereof, and constitutes a third plane of symmetry at least for the bending zone, which is also frequently the case, e.g. if the testpiece is in the form of a rectilinear rod of constant section as corresponds to the most frequent case of testpieces that are in the form of a plate that is flat or curved:

step b) is implemented in such a manner that the third mean planes of the two testpieces coincide and the pivot axes are mutually symmetrical about the third mean planes which thus coincide; and for the machine of the invention, when the slots of each pair of clamps in the rest position present respective third mean planes which are perpendicular to their first mean planes and on either side of which they are disposed, the third mean planes of the two sets of said pairs are mutually symmetrical about the point or center of symmetry when the two sets of clamps are in the rest position, said mutual symmetry of the third mean planes of the two sets of the pairs of clamps including the special case in which the third mean planes coincide and include the point or center of symmetry.

Various methods of connecting each of the grip zones to the corresponding pivot axis can be envisaged, but it is preferred to use a connection that is as direct as possible, so as to avoid inducing interfering forces between each testpiece and the means for measuring the bending resistance opposed to the turning movement by the bending zone of each of them.

In this respect, in a preferred implementation of the method of the invention, step b) is implemented by connecting each of the grip zones to the corresponding respective pivot axis by an arm, the arms corresponding to the grip zones of the two testpieces being mutually symmetrical about said point, and by connecting the two arms corresponding to a given pivot axis by means of a respective controlled motor suitable for imparting optionally alternating opposing turning movements to the two arms about the corresponding pivot axis, the controlled motors corresponding to the two pivot axes being mutually identical and being allowed to move freely relative to each other.

To this end, and respectively for each of the motor assemblies of the machine of the invention:

the means for defining the relative pivot axes of the two clamps comprise:

two shafts mounted on the same axis to turn relative to each other about the relative pivot axis; and two arms, each of which secures one of the clamps to a respective one of the shafts; and the controlled motor means for imparting relative optionally alternating turning movement to the clamps about the relative pivot axes, comprise a controlled motor that is mechanically independent of the control motor of the other motor assembly and that is suitable for imparting relative, optionally alternating turning movements to the two shafts, such that the test apparatus of the invention is then characterized in that:

the means for defining the pivot axes of the two sets comprise:

on each of the pivot axes, two respective shafts on the same axis and mounted to turn relative to each other about the corresponding pivot axis; and four arms that are mutually symmetrical about said point, each connecting a respective one of the shafts to a respective one of the clamps corresponding to the same pivot axis; and the controlled motor means for applying opposing, optionally alternating torques about each pivot axis to the corresponding clamps comprise two mutually identical controlled motors arranged in such a manner as to be capable of moving freely relative to each other, each of the motors being associated with a respective one of the pivot axes and being suitable for imparting opposing, optionally alternating turning movements to the two respective corresponding shafts, with each of the controlled motors advantageously being constituted by an electric stepper motor, in particular for the purpose of facilitating selection of the pivot amplitude of each clamp, i.e. of each grip zone, about the respective pivot axis relative to the clamp and to the grip zone corresponding to the same pivot axis, i.e. making it easier to adjust the bending amplitude for each of the bending zones, even though other means may be selected for this purpose.

It is then possible to measure the resistance opposed to turning by at least one of the grip zones of at least one of the testpieces by measuring the twisting stresses on at least one of the shafts of at least one of the motor assemblies, in which case it is possible to choose to make each arm in such a manner that it is rigid in bending in any mean plane and also in twisting.

Nevertheless, it is preferred to ensure that each arm is elastically bendable in the first mean plane of the corresponding testpiece, i.e. in the first mean plane of the slot of the corresponding clamp, i.e. in a mean plane perpendicular to the corresponding pivot axis, with stiffness that is greater than the stiffness of the bending zone of the testpiece, while being rigid otherwise, thus making it possible to measure the bending stresses to which at least one of the arms is subjected in a direction that is circumferential relative to the corresponding pivot axis, which bending stresses are much more directly representative of the bending resistance of the bending zone, in which case the measurement means comprise means for measuring the bending stresses to which at least one of the arms is subjected in said mean plane.

For this purpose, it may be tempting to measure the bending stresses to which each of the arms is subjected, by providing appropriate measurement means on each of them, however testing to validate the method of the invention and performed on an apparatus and a machine of the invention has shown that measuring the bending stresses to which only one of the arms is subjected gives a result that is meaningful and that has sufficient accuracy concerning the resistance to bending of the bending zone in each of the testpieces, and concerning changes in said bending resistance as alternating bending progresses, i.e. when performing fatigue testing in bending.

In order to make it easier to measure the bending stresses to which at least one of the arms is subjected, it is preferable to provide for each of the arms to present at least one zone that is weakened in bending in said mean plane perpendicular to the corresponding pivot axis, i.e. in a direction that is circumferential relative to said corresponding pivot axis, with the zones thus weakened in bending being mutually symmetrical about the point or center of symmetry, and with the means for measuring the bending stresses of at least one of the arms being placed in said zone.

As the person skilled in the art will readily understand, the symmetry in the treatment given to the two testpieces and in the apparatus of the invention about a point or center of symmetry while the testpieces are in their rest state and the clamps are in their rest position is characteristic of the present invention and can be obtained in two main manners, by appropriately arranging the arms, the shafts, and the motors.

This arrangement may be such that in the rest state of the testpieces and in the rest position of the clamps:

- the pivot axes are mutually parallel and disposed respectively on either side of the point or center of symmetry, in which case, if each testpiece in its rest state presents a third mean plane as specified above and if said mean plane constitutes not only a plane of symmetry for the bending zone but also a plane of mutual symmetry for the grip zones, the arms corresponding to the grip zones of the two testpieces may advantageously be mutually identical; or else
- the pivot axes coincide and pass through the point or center of symmetry, this relative positioning being considered as constituting a special case of mutual symmetry for the pivot axes about the point or center of symmetry in the meaning of the present invention.

In both cases, the machine and the apparatus of the invention may be very simple to implement, such that in spite of using two motors, the cost price remains competitive compared with that of prior art apparatuses, and reliability is, in contrast, considerably increased.

Although as stated above, testpieces of very different shapes can be subjected to bending tests in accordance with the present invention, each testpiece is made or selected during step a) of the method of the invention in such a manner as to present the shape of a plate of thickness that extends perpendicularly to its mean surface, in which case:

- said thickness is preferably constant, at least in the bending zone;
- each testpiece preferably presents a dimension that is constant perpendicularly to the first mean plane, at least in the bending zone; and
- each testpiece preferably presents a respective transition perpendicular to the first mean plane between the bending zone and each of the grip zones.

A testpiece as made in this way in the form of a plate is particularly suitable for bending tests of large amplitude, and in order to be able to access bending amplitudes of about 90° between the grip zones, it is preferable to provide for the clamps of the machine or the apparatus of the invention to be chamfered so as to taper towards each other, when the clamps are seen in the rest position.

Other characteristics and advantages of the various aspects of the present invention appear from the description below relating to two non-limiting implementations, and also from the accompanying drawings which form an integral portion of the description.

BRIEF DESCRIPTION OF THE DRAWINGS

FIGS. 1 and 2 are perspective views showing a non-limiting example of the shape of a testpiece suitable for use in implementing the method of the invention, the testpiece in this non-limiting example being generally in the shape of a flat plate, e.g. obtained by being cut out from a flat metal sheet, and prepared in two different ways in order to enable it to be integrated in test apparatus of the invention.

FIG. 3 is a diagrammatic side elevation view of apparatus for implementing the method of the invention, comprising a machine of the invention and two mutually identical testpieces, e.g. as shown in FIG. 1 or in FIG. 2, or indeed having any other shape suitable for enabling a bending test to be performed, the apparatus being shown in a rest position with the two testpieces being in the rest state.

FIG. 4 is a view from above seen looking along the direction identified by IV in FIG. 3, showing the same apparatus likewise in the rest position with the two testpieces being in the rest state.

FIG. 5 is a view from above similar to that of FIG. 4, showing the apparatus after it has left its rest position and the two testpieces have been subjected to bending in opposing manners.

FIGS. 6 to 8 are diagrammatic views similar to FIGS. 3 to 5 respectively, showing apparatus having a variant embodiment of the machine, FIG. 7 being a view from above seen looking along VII of FIG. 6.

FIG. 9 is a side elevation view similar to that of FIG. 6 showing a concrete embodiment of the apparatus shown in FIG. 6 while in the rest position with the two testpieces being in the rest state.

FIG. 10 is a view from above seen looking in a direction referenced X in FIG. 9, showing how surface deformation gauges are positioned on a zone of one of the arms of the apparatus that is a zone of weakness in bending, the gauges constituting means for measuring the bending stresses to which said arm is subjected because of the strength of the two testpieces in bending.

FIG. 11 is a connection diagram of the apparatus.

FIG. 12 is a perspective view of the apparatus shown in FIG. 9, the apparatus being in the rest position with the testpieces being in the rest state.

FIGS. 14 and 15 are perspective views showing respectively one of the mutually identical arms of the machine and a variant embodiment of one of these mutually identical arms.

FIGS. 16 and 17 are perspective views showing the two jaws of one of the mutually identical clamps of the test machine of the invention in a shape adapted to the shape of the testpiece shown in FIG. 1 or in FIG. 2, it being understood that each shape of testpiece to be tested in bending corresponds to a clamp having a specific shape, as will easily be designed by a person skilled in the art as a function of the shape of the testpiece.

FIG. 19 is a diagrammatic elevation view similar to that of FIGS. 3 and 6 showing another embodiment of apparatus of the invention in the rest position with the two testpieces being in the rest state.

FIGS. 20 and 21 are views of the apparatus in section on planes marked XX—XX and XXI—XXI in FIG. 19, showing the two testpieces in the rest state while the apparatus is in the rest position.

FIGS. 22 and 23 are views similar to those of FIGS. 20 and 21, respectively, with the two testpieces being in the oppositely-bent state, e.g. being bent through a right angle, the apparatus having left its rest position.

DETAILED DESCRIPTION OF THE INVENTION

Figure 13:
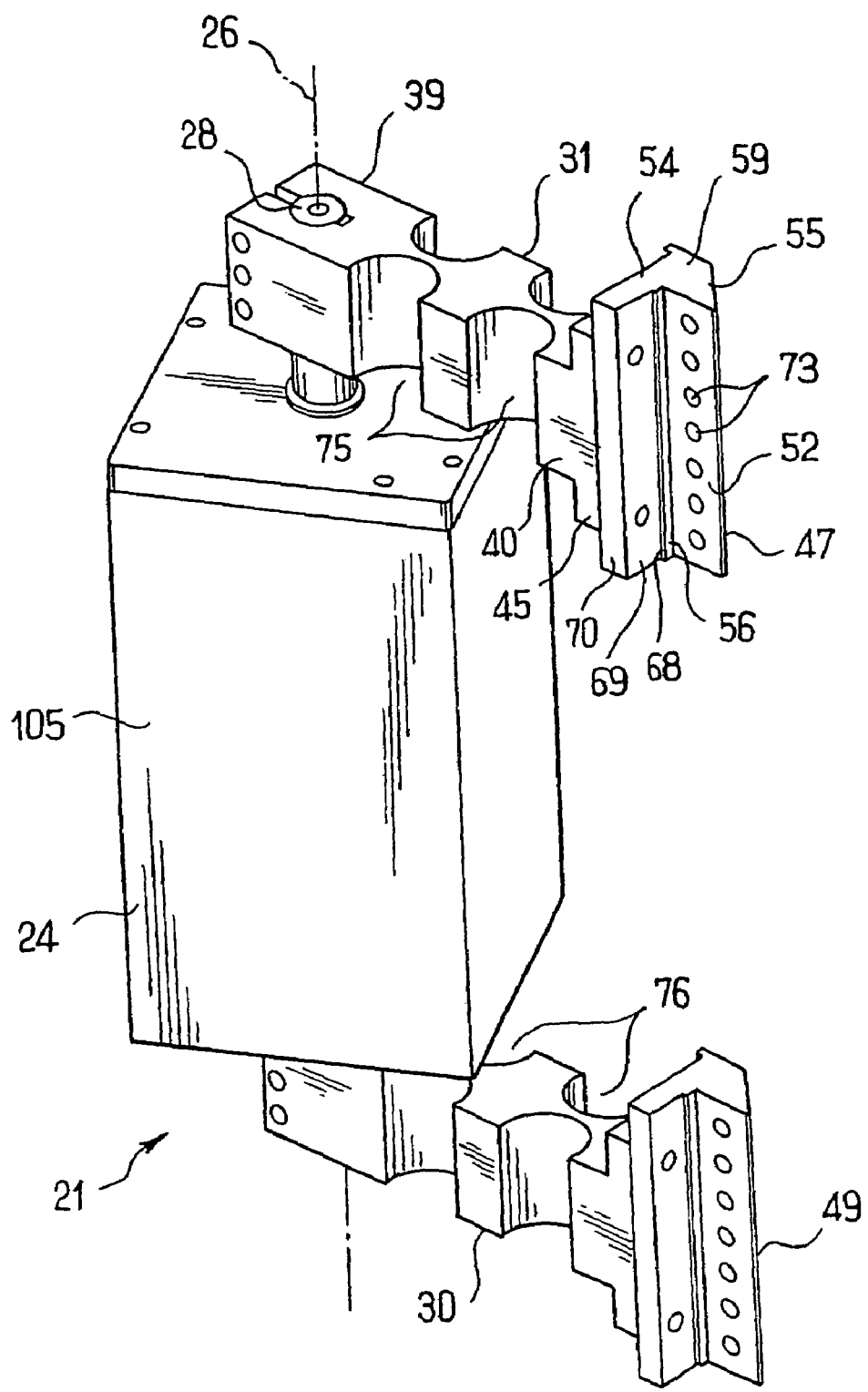
FIG. 13 is a perspective view of one of the two mutually identical motor assemblies constituting the test machine of the invention in this case.

Reference is made initially to FIG. 1 which shows a testpiece 1 in the rest state, i.e. when subjected to no stress, in particular no bending stress, and comprising a bending zone 2 for being subjected to the alternating bending test, between two end grip zones 3 and 4 which are not themselves subjected to any bending during testing.

The bending zone 2 presents a first mean plane 5 of symmetry crossing each of the zones 2, 3, and 4 and also constituting a first mean plane of symmetry for the grip zone 4, and a mean surface which is perpendicular to said first mean plane 5 and which, in this example, is plane and constitutes a second mean plane of symmetry 6 for each of the zones 2 and 4, and a mean plane of symmetry for the zone 3. In this example, the bending zone 2 presents a third mean plane of symmetry 7 that it crosses and that intersects the mean planes 5 and 6 at right angles, the grip zones 3 and 4 being disposed respectively on either side of this mean plane 7. In this example, the grip zone 3 is asymmetrical relative to the first mean plane 5 and is not symmetrical to the grip zone 4 about the third mean plane 7, but it could likewise present its own symmetry relative to the first mean plane 5 and it could be symmetrical to the grip zone 4 relative to the third mean plane 7, the shapes of the grip zones 3 and 4 being of little importance with respect to the bending test which is applied only to the bending zone 2.

In each of the three zones 2, 3, and 4, the testpiece 1 is defined by two main faces such as 8 which, in this example, are plane, and mutually parallel, and also parallel to the second mean plane 6 about which they are symmetrical relative to each other, which main faces such as 8 define between them a thickness $\underline{e}$ of the testpiece, which thickness $\underline{e}$ is measured perpendicularly to the second mean plane 6 and presents a value that is constant, in particular in the bending zone 2. The two main faces such as 8 are connected together by an edge face 9 perpendicular to the second mean plane 6, which edge face 9 is of rectangular shape that is elongate perpendicular to the first mean plane 5 in each of the zones 2, 3, and 4, both in the second mean plane 6 and in any section plane parallel thereto. The bending zone 2 presents a length $L_1$ perpendicularly thereto that is shorter than the length $L_2$ that the grip zone 4 presents perpendicularly to said mean plane 5, which is itself shorter than the length $L_3$ that the grip zone 3 presents perpendicularly to said plane, such that the testpiece 1 presents a marked transition between each grip zone 3, 4 and the bending zone 2, this transition being embodied by respective zones 107 of the edge face 9 that are perpendicular to the first mean plane 5, defining the grip zones 3 and 4 beside the third mean plane 7 and facing said mean plane respectively at opposite ends of the bending zone 2 and on either side of the first mean plane 5.

The two grip zones 3 and 4 are pierced by respective mutually identical through holes 12 and 13 that are circularly cylindrical about respective axes 10, 11 perpendicular to the second mean plane 6 and mutually symmetrical about the third mean plane 7, i.e. the holes interconnect the main faces such as 8 inside the edge face 9. The points of intersection 14, 15 between the axes 10, 11 and the second mean plane 6 are regularly distributed along respective alignments (not shown) perpendicular to the first mean plane 5, about which they are likewise symmetrically distributed; in other words, for an odd number of holes 12 and of holes 13 in the non-limiting example shown, where said number is 7, one of the axes 10 and one of the axes 11 lie in the first mean plane 5 while the other axes 10, 11 are disposed mutually symmetrically about said first mean plane 5.

The testpiece 1 having this shape may be cut out from the sheet metal to be tested using any suitable means leading firstly to as little internal stress as possible and secondly to as small as possible a risk of changing bending behavior, e.g. by changing crystal structure; for this purpose, it is indeed possible to cut out the testpiece 1 and to make the holes 12 and 13 therein using techniques that involve a tool coming into contact with the sheet metal, such as stamping, however it is preferred to use techniques that do not involve any contact between a tool and the sheet metal, such as electro-erosion, or laser cutting, or water-jet cutting.

In order to simplify the making of a testpiece 1 by electro-erosion, when it comes to making the holes 12 and 13, the testpiece may be shaped in the manner shown in FIG. 2, i.e. with each of the holes 12 and 13 in the corresponding respective grip zone 3 or 4 being connected to the edge face 9 of the testpiece 1 via a respective slot 16, 17 which leaves the corresponding hole 12, 13 and extends perpendicularly away from the mean plane 7 so as to open out into a zone of the edge face 9 parallel to said mean plane 7 and defining the boundary of a respective one of the grip zones 3 and 4 going away from said plane. Each of the slots 16 and 17 also opens out into both of the main faces such as 8 so that the edge face 9, the slots 16 and 17, and the holes 12 and 13 can be made in a single continuous path of the electro-erosion electrode around a closed outline. The testpiece 1 otherwise remains identical to that described with reference to FIG. 1, and in particular its bending zone 2 is not in any way affected by the presence of the slots 16 and 17, in particular its bending behavior between the grip zones 3 and 4 is not affected.

In a manner characteristic of the present invention, two identical testpieces 1, or testpieces having some other shape, are subjected simultaneously to the alternating bending test by being subjected to alternating bending in mutually opposite directions at all times in apparatus presenting as few mechanical connections as possible with a support structure, such that each testpiece bends in its bending zone 2 under conditions that are as close as possible to pure bending conditions. Two testpieces are said herein to be "identical" when it is to be expected that their behavior in terms of bending in their bending zones 2 will be identical, and in particular that changes in the bending zone 2 due to bending fatigue are identical, with this generally being the result of the testpieces being geometrically identical.

To this end, a test apparatus is used, with a first embodiment being shown in a first variant 18 in FIGS. 3 to 5 and in a second variant 19 in FIGS. 6 to 18, and with another embodiment 20 being shown in FIGS. 19 to 24.

Reference is made initially to FIGS. 3 to 5 which show apparatus 18 of the invention comprising two motor units 12 that are mutually identical, both structurally and functionally, that are disposed opposite ways round, that are symmetrical to each other about a point or center of symmetry 22, and that are mechanically interconnected by the two testpieces 1, themselves disposed symmetrically to each other about the point 22. In order to get as close as possible to an ideal situation in which the two testpieces 1 constitute the sole mechanical connection between the two motor assemblies 21, these assemblies are suspended from a support structure 23 which is disposed at a level that is as high as possible, suspension being via ties 29 that are as long and as flexible as possible so as to carry the weight of the motor assemblies 21 while delivering as little force as possible to the two testpieces 1 themselves alone providing the mechanical connection between the two motor assemblies 21.

More precisely, each motor assembly 21, which is advantageously constituted by an electrical stepper motor, comprises a stator 24 having a rotor 25 guided to turn therein about an axis 26 without having any other possibility of relative displacement. Each motor assembly 21 presents along said axis 26 two mutually opposite outlet shafts 27 and 28, the first being secured to the stator 24 and the second to the rotor 25, so that the two shafts can thus turn relative to each other on the same axis in either direction depending on how electricity is supplied to the motor assembly 21. Given the above-specified symmetry of the motor assembly 21 relative to the point 22, the vertically extending axes 26 are disposed respectively on either side of said point 22 and the shafts 27 and 28 of one of the motor assemblies 21, i.e. the assembly that is on the right in FIGS. 3 and 5, point respectively upwards and downwards, while the shafts 27 and 28 of the other motor assembly 21, i.e. situated on the left in FIGS. 3 to 5, point respectively downwards and upwards. The upwardly-pointing shafts 27 and 28 of the motor assemblies 21, i.e. the shaft 27 of the right-hand motor assembly 21 and the shaft 28 of the left-hand motor assembly 21, carry means at their top ends (such as respective link rings) for securing to respective corresponding bottom ends of the flexible ties 29, whose own top ends are secured to the support structure 23, e.g. by being suspended from respective hooks thereon, with this taking place under conditions such that the two flexible ties 29 are at least approximately vertical and are disposed at least approximately along the respective corresponding axes 26 when the apparatus 18 shown in FIGS. 3 and 4 is in a rest position corresponding to the two testpieces 1 being in a rest state.

Remote from its respective connection with the stator 24 or the rotor 25, each of the shafts 27, 28 is secured to a respective rectilinear arm 30, 31 extending radially relative to the corresponding axis 26 and ensuring that the two motor assemblies 21 are mutually symmetrical about the point 22 in the sense that the two arms 30 corresponding to the shafts 27 are identical and mutually symmetrical about the point 22, as are the two arms 31 corresponding to the shafts 28, and the arms 30 and 31 are advantageously also mutually identical.

Going away from the corresponding shaft 27, 28 and the respective axis 26, each of the arms 30, 31 is secured to a respective clamp 32, 33, the clamps 32 and 33 themselves being identical and complying with the above-specified mutual symmetry about the point 22.

In the rest position of the motor assemblies 21, as shown in FIGS. 3 and 4, the clamps 32 and 33 face each other in pairs, with the clamps 32 and 33 of one pair securely holding respective grip zones 3 and 4 of one of the testpieces 1 such that only the bending zone 2 is free between them and capable of bending between them. Preferably, each of the clamps 32 and 33 can be clamped equally well onto one or other of the grip zones 3, 4 of a testpiece 1.

Thus, the two clamps 32 and 33 corresponding to the arms 30 and 31 themselves corresponding to the upwardly-pointing shafts 27 and 28 securely receive respective grip zones 3 and 4 of one of the testpieces 1 while the two clamps 32 and 33 corresponding to the arms 30 and 31 themselves corresponding to the downwardly-pointing shafts 27 and 28 securely carry respective grip zones 3 and 4 of the other testpiece 1.

The two motor assemblies 21 are designed in such a manner that in a rest position corresponding to the rest state of the testpieces 1:

the mean planes 6 of symmetry thereof coincide and contain both the two axes 26 and the point or center of symmetry 22;
  the mean planes of symmetry 7 coincide, include the point or center of symmetry 22, and constitute a mean plane of symmetry between the axes 26 that are disposed respectively on either side of the coinciding planes 7 and that extend parallel thereto; and
  the mean planes of symmetry 5 are mutually parallel, perpendicular to the two axes, and disposed respectively above and below the point 22, and are mutually symmetrical about said point.

This rest position and state are shown in FIGS. 3 and 4.

Starting from the rest position of the motor assembly 21, it is possible, by appropriately controlling the motors, to cause their rotors 25 to turn relative to their stators 24 through identical amplitudes and in identical directions such that the two clamps 32 and 33 connected to the upwardly-pointing shafts 27 and 28 move in the same direction relative to the clamps 32 and 33 corresponding to the downwardly-pointing shafts 27 and 28, as shown in FIG. 5, thus causing the bending zones of the two testpieces 1 to bend in opposite directions, and since the testpieces are identical, as specified above, this results in the apparatus 18 overall, i.e. including both the two motor assemblies 21 and the two testpieces 1, retaining its symmetry about the point 22.

Thereafter, turning the shafts 28 of the two motor assemblies 21 simultaneously in the directions opposite to the preceding directions relative to the motor shafts 27 causes these two assemblies 21 to return to the rest position and the two testpieces 1 to return to the rest state and, by then continuing through an amplitude identical to the preceding amplitude, causes each of the testpieces 1 to bend in the direction opposite to the preceding direction, with continued controlled alternating turning movements of the outlet shafts 28 of the two motor assemblies 21 relative to the outlet shafts 27 causing the two testpieces 1 to be bent in alternation under conditions that are substantially identical, while preserving symmetry about the point 22 to within a good approximation.

Naturally, the alternating bending of the two testpieces 1, that accompanies the alternating relative turning movements of the two arms 30 and 31 of each of the motor assemblies 21, is accompanied by alternating movement whereby the two axes 26 move towards each other and apart from each other, which axes remain parallel because symmetry is preserved relative to the point 22, thereby causing the two flexible ties 29 to oscillate about their top ends that are secured to the top structure 23. Nevertheless, the greater the length of the flexible ties 29, the smaller the amplitude of such oscillations and the smaller the interfering forces induced in the bending zones 2 of the two testpieces 1 by the relative movements between the two axes 26, i.e. the two motor assemblies 21. It can be considered to within a good approximation that the axes 26, or indeed the motor assemblies 21, are completely free to move relative to each other.

In accordance with the present invention, during the alternating opposite bending operations applied to the two testpieces 1 under drive from the suitably-controlled motor assemblies 21, the substantially identical resistance of each of the bending zones 2 is measured in order to study how this resistance changes, by measuring the resistance against the alternating turning about the corresponding axis 26 that is opposed by at least one of the grip zones 3, 4 of at least one of the testpieces 1, i.e. by at least one of the clamps 32 and 33. To this end, and preferably, the bending stresses suffered by at least one of the arms 30 and 31 are measured under conditions that are completely identical to those which are described below with reference to the apparatus of the invention 19 shown in FIGS. 6 to 18, to which reference is now made.

If reference is made initially to FIGS. 6 to 8, it can be seen that the apparatus 19 implements the same means as the apparatus 18, except that instead of the two motor assemblies 21 being disposed opposite ways round so as to be rigorously symmetrical to each other about the point 22, the two motor assemblies 21 are both disposed in the same orientation, such that both shafts 27 point in the same direction and likewise both shafts 28, with the axes 26 nevertheless remaining vertical and being disposed respectively on opposite sides of the point 22 and symmetrically to each other about said point.

More precisely, in the example shown, the two shafts 27 point downwards and the two clamps 32, each connected to a respective one of the shafts 27 by a respective arm 30, points towards the other in the rest position and is secured firmly to a respective one of the grip zones 3, 4 of one of the testpieces 1 under conditions such that only the bending zone 2 thereof is free to bend between them, while both shafts 28 point upwards and the respective clamps 33 connected to said shaft 28 by respective arms 31 face each other in the rest position and are firmly secured to respective ones of the grip zones 3 and 4 of the other testpiece 1 in the rest state in conditions such that only the bending zone 2 is free to bend between them. Under such circumstances, it is the shafts 28 that have their ends remote from the respective rotors 25 secured to a flexible tie 29 for suspension from the support structure 23.

Naturally, it would be equally possible for the shafts 27 to point upwards and be used for suspending the corresponding motor assembly 21 from the support structure 23.

Even through the stators 28 and the rotors 25 of the two motor assemblies 21 do not comply structurally with the symmetry about the point 22 as shown in the case of the apparatus 18, each of the arms 31 is symmetrical to a respective one of the arms 30 about the point 22 and likewise both testpieces 1 are mutually symmetrical about said point 22, in particular on referring to the rest position and the rest state, in the case of the apparatus 19, which means that it is functionally symmetrical about the point 22 and operates in equivalent manner to the apparatus 18, i.e. is just as suitable for imparting alternating opposite bending actions to the two testpieces 1.

Nevertheless, for this purpose, it is necessary to offset the two arms 31 angularly about the axis 26 in the same alternate direction relative to the arm 30, starting from the rest position, i.e. it is necessary to turn the shafts 28 in mutually opposite directions relative to the respective corresponding shaft 27, as shown in FIG. 8. The functional mutual symmetry of the two motor assemblies 21 about the point 22, and the mutual symmetry of the two testpieces 1 about said point 22 are conserved under the same conditions as for the apparatus 18, as will readily be understood by the person skilled in the art.

Figure 18:
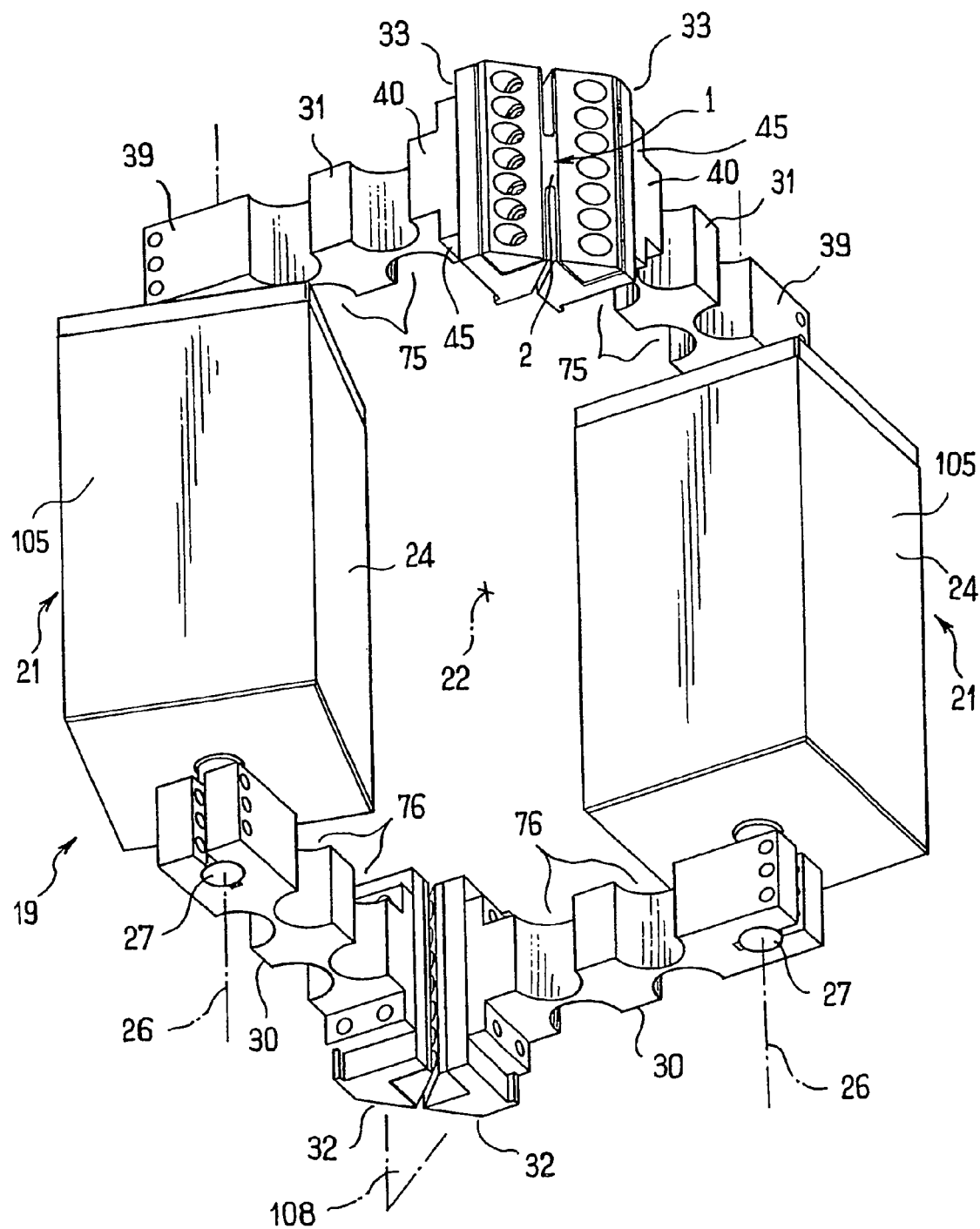
FIG. 18 is a perspective view of the apparatus after it has left the rest state, the two ends of the testpiece being in the oppositely-bent state, e.g. being bent through a right angle.
Figure 24:
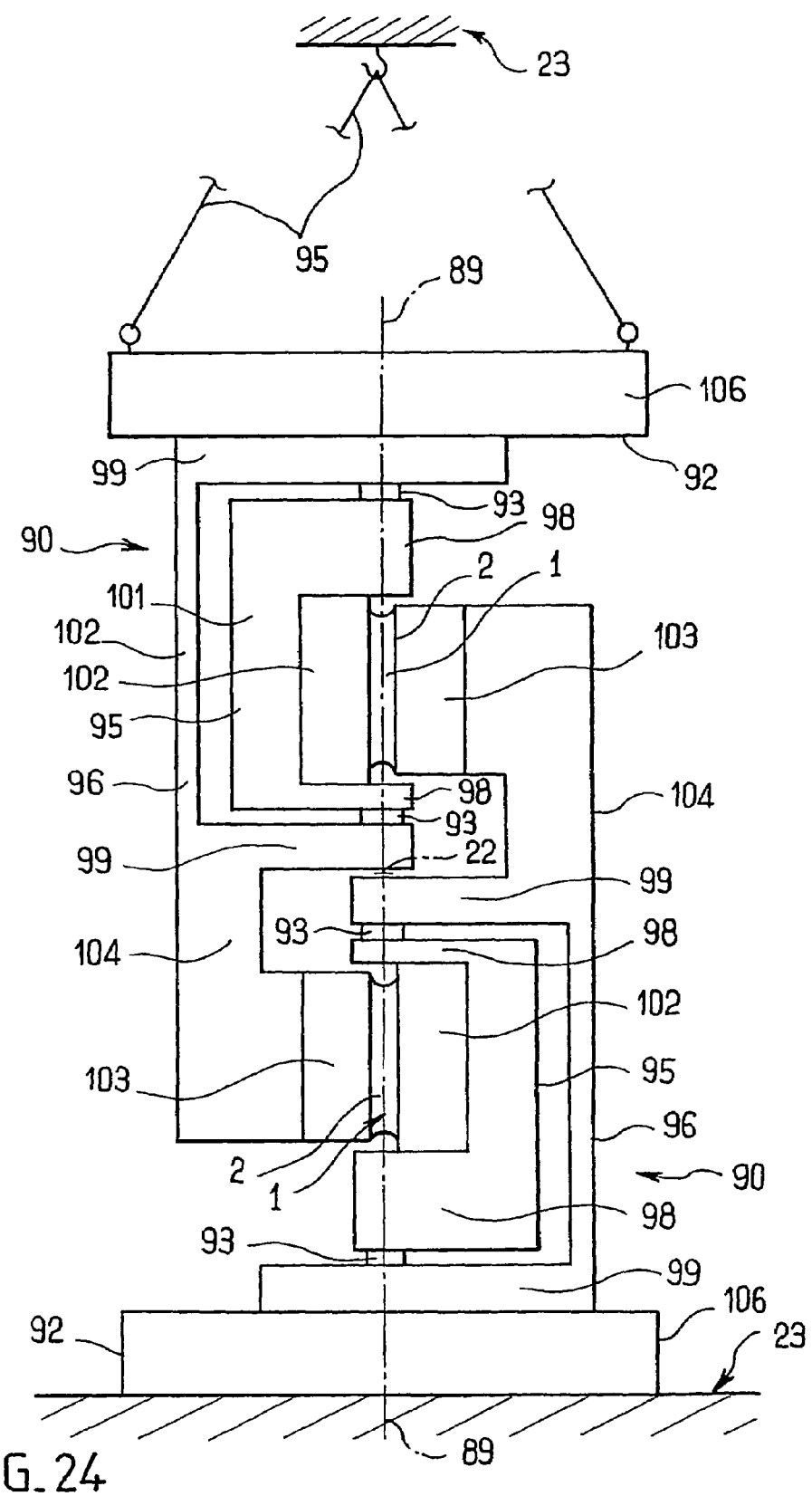
FIG. 24 is a side elevation view similar to that of FIG. 19 showing a concrete embodiment of the apparatus of the invention in the case of this variant, with the apparatus being shown in the rest position and the two testpieces in the rest state.

FIGS. 9, 12, and 18 show a practical embodiment of the apparatus 19, while FIG. 13 shows the practical embodiment of one of the motor assemblies 21.

The various components described with reference to FIGS. 6 to 8 or, by analogy, with reference to FIGS. 3 to 5 are to be found therein with the same numerical references, and for the sake of simplicity certain practical embodiment details are described below with reference to the apparatus 19 being in the rest position as shown in FIGS. 9 and 12 in particular, unless specified to the contrary.

If reference is also made to FIG. 14, which shows an arm 31, it being understood that the arms 30 and 31 are identical in the preferred embodiment shown, it can be seen that such an arm presents two mean planes of symmetry 34 and 35, the first of which contains the corresponding axis 26 and the second of which is perpendicular to said axis. These two mean planes of symmetry 34 and 35 coincide respectively with the mean planes of symmetry 6 and 5 of the corresponding testpiece 1 when the apparatus 19 is in the rest position and the two testpieces 1 are in the rest state.

The arm 31 presents a mean fiber 36 that is rectilinear, as defined by the line of intersection of the planes 34 and 35, and intersects the corresponding axis 26 perpendicularly, and the arm 31 presents a shape that is elongate in a direction defined by said mean fiber 36, perpendicularly to which the arm 31 presents a constant square running section defined by two plane rectangular faces 27 parallel to the plane 35 and mutually symmetrical thereabout, and by two likewise rectangular plane faces 38 parallel to the plane 34 and mutually symmetrical thereabout.

With reference to a direction defined by its mean fiber 36, the arm 31 presents two mutually opposite end zones 39, 40, the first of which is shaped in such a manner as to be secured to the shaft 28 of the corresponding motor assembly 21 and the other of which is free and fastened securely to the corresponding clamp 33.

In order to secure the arm 31 to the shaft 28, the end zone 39 presents a slot 41 in the plane 34, said slot opening out into an end face 42 of the arm 31, which face is perpendicular to the mean fiber 36, and also into zones of faces 37 that are directly adjacent to said face 42, and the slot 41 presents locally at 43 a shape that is complementary to the corresponding shaft 28 so as to be engaged snugly thereabout in the required position for the planes 34 and 35 relative to the axis 26. Between the shape 43 in the slot 41 and the end face 42, housings 44 are provided perpendicularly to the plane 34 for receiving tightening screws which, by tending to close the slot 41, ensure intimate mutual compression contact between the arm 31 and the shaft 28 so as to achieve the locked-for mutual connection.

The other end zone 40 of the arm 31, i.e. the free end of said arm, is shaped to present a connection flange 45 that is releasably secured to the corresponding clamp 33, thereby enabling the clamp to be interchanged in order to adapt the apparatus to testpieces 1 of different shapes.

The way in which each arm 30 is secured to the corresponding shaft 27 and in which the corresponding clamp 32 is securely but releasably received thereby are identical to that described above.

With reference to the testpiece shape described with reference to FIGS. .1 and 2, each clamp 33 (to which each clamp 32 is identical) is designed in such a manner as to define a reception slot 46 that is releasably secured on one of the grip zones 3, 4 of the corresponding testpiece 1 by clamping said zone between two jaws 47 and 48, the first of which is secured securely but releasably to the arm 31 via the flange 45 and the other of which is secured securely but releasably to the first. Likewise, each clamp 32 is constituted by a jaw 49 secured securely but releasably to a flange-forming free end zone of the corresponding arm 30, and a jaw 50 secured securely but releasably to the jaw 49, the jaws 49 and 50 defining between them a slot 51 for securely but releasably receiving one of the grip zones 3 or 4 of the corresponding testpiece 1 by said jaws being tightened together. Since the four clamps 32 and 33 are mutually identical, only one of these clamps is described below, namely one of the clamps 33, with reference also being made to FIGS. 16 and 17, which show both of the jaws 47 and 48 thereof.

For a testpiece 1 having the shape described with reference to FIGS. 1 and 2, the slot 46 of the clamp 43 is defined by two plane clamping faces 52 and 53, the first of which is defined by the jaw 47 and the second by the jaw 48 and which are disposed respectively on either side of the plane 34, being parallel thereto and mutually symmetrical thereabout, while they are also respectively symmetrical about the plane 35, as is the case for each of the jaws 47 and 48 considered as a whole.

Each of the jaws 47, 48 is made as a single respective rigid piece, e.g. made of steel.

The jaw 47 presents two portions 54 and 55, the first of which constitutes a mounting stock that is releasably secured to the end flange 45 of the arm 31, e.g. by bolting, and preferably with localized mutual engagement, with design of the respective shapes of the portion 54 and of the flange 45 for this purpose forming part of the normal skills of a person skilled in the art.

Opposite from the flange 45 and the arm assembly 31 in a direction defined by the mean fiber 36 thereof, the portion 54 presents a plane face 56 perpendicular to the mean fiber 36 and symmetrical about the two planes 34 and 35, both of which it crosses, presenting a dimension equal to $L_2$ perpendicularly to the plane 34. In general, the jaw 47, like the jaw 48, is symmetrical about the plane 34 and presents the dimension $L_2$ perpendicularly thereto.

Perpendicularly to the plane 35, the face 56 presents a dimension E that is greater than e and that is distributed asymmetrically relative to the plane 35, on either side thereof, i.e. by an amount equal to half of e on one side of the plane 35, situated below said plane 35 in FIG. 16, and for the remainder on the other side of said plane 35, situated above the plane 35 in FIG. 16.

From the first of the above-specified sides of the plane 35, i.e. from a distance therefrom equal to half of e, the face 56 is connected to the face 52 which is parallel to the plane 35 and is thus spaced apart therefrom by a distance equal to half of e, and projects away from the corresponding arm 31 in the direction defined by the mean fiber or intersection 36 between the two planes 34 and 35 thereof, relative to the stock portion 54, defining the portion 55 towards the plane 35.

The face 52 is plane and rectangular, its dimensions in the plane being substantially identical to those of the portion of one of the main faces 8 of the testpiece 1 that correspond to the grip zone 4. In other words, it presents the dimension $L_2$ perpendicularly to the plane 34 whereas in the direction defined by the mean fiber or intersection 36 between the planes 34 and 35 it presents a dimension $l_1$ identical to the dimension that the grip zone 4 or the grip zone 3 presents perpendicularly to the plane 7, likewise identified by $l_1$. Thus, the grip zone 4 of the testpiece 1 or equally well a portion 57 of the grip zone 3 of said testpiece 1 (which portion 57 constitutes the specular image of the grip zone 4 about the mean plane of symmetry 7 of the testpiece 1 and is distributed symmetrically on either side of the mean plane of symmetry 5 thereof) can be pressed flat in full via one of the main faces 8 of the testpiece 1 against the face 52 while the testpiece is also pressed flat via a zone of its edge face 9 opposite from the other grip zone, respectively 3 or 4, against the face 56 of the jaw 47 from which said other grip zone and the bending zone 2 remain clear. If the grip zone as pressed via one of its main faces 8 against the face 52 is the grip zone 3 that presents a length $L_3$ greater than the length $L_2$, the portion 58 other than the portion 57 projects beyond the jaw 47 in a direction perpendicular to the plane 34 relative to one of the two plane faces 59 that are parallel to the plane 34 and mutually symmetrical thereabout and mutually spaced apart by said length $L_2$, which faces 59 define the two portions 54 and 55 of the jaw 47 and all of their other faces, going away from the plane 34.

When going away from the face 56 in the direction defined by the mean fiber or intersection 36 between the two planes 34 and 35, the face 52 of the jaw 47 meets a face 61 of the portion 55 of the jaw 47 via a skew rectilinear edge 60 perpendicular to the plane 34 and symmetrical thereabout, to a face 61 of the portion 55 of the jaw 47, which face 61 is plane, perpendicular to the plane 34 and symmetrical thereabout, and slopes, e.g. at about 45°, relative to the plane 35 and to the face 52 so as to form a chamfer relative thereto. In other words, the portion 55 of the jaw 47 tapers progressively between the faces 52 and 61 going towards the edge 60.

Going away from said edge 60, which amounts also to going away from the face 52 and the plane 35, the face 61 is connected via a rectilinear edge (not referenced) perpendicular to the plane 34 to a face 62 parallel to the plane 35 and common to both portions 54 and 55 of the jaw 47 and defining it going away from the plane 35.

The jaw 48 shown more particularly in FIG. 17 and diagrammatically as a chain-dotted line in FIG. 16 when in the position that it occupies relative to the jaw 47 while the two jaws 47 and 48 are holding securely between them a grip zone 3 or 4 of a testpiece 1, presents a shape such that it then corresponds at least approximately to a specular image of the portion 55 of the jaw 47 about the plane 35.

In the direction going away from the plane 34, the jaw 48 is defined by two plane faces 63 parallel to the plane 34 and mutually symmetrical about said plane, which faces 63 are spaced apart mutually by the distance $L_3$ perpendicularly to said plane and define, going away therefrom, all of the other faces of the jaw 48 that are described below, including its face 53 that co-operates with the face 52 of the jaw 47 to define the slot 46.

The face 53 presents dimensions that are identical to those of the face 52 which it is placed facing in a direction perpendicular to the plane 35, and it is connected via a skew straight edge 64 perpendicular to the plane 34 and symmetrical to the skew edge 60 about the plane 35 when the jaws are holding between them the grip zone 3 or 4 of a testpiece 1, to a plane face 65 perpendicular to the plane 34 and which defines a chamfer relative to the face 53, being symmetrical to the face 61 relative to the plane 35. On going away from the edge 64 and the face 53, and also relative to the plane 35, this face 65 is connected via a straight edge perpendicular to the plane 34 to a plane face 66 perpendicular to the plane 34 and occupying apposition that is symmetrical to that of the face 62 about the plane 35 so as to define the jaw 48 in the direction going away from said plane 35. On going away from its connection with the face 65, in a direction defined by the mean fiber or intersection 36 between the planes 34 and 35, the face 66 nevertheless presents a size that is smaller than that of the face 62 and is connected via a straight edge perpendicular to the plane 34 to a plane face 67 perpendicular to the two planes 34 and 35 and connecting to the face 53 via a straight edge perpendicular to the plane 34 going towards the plane 35. By means of this face 67, i.e. more particularly by a zone of this face 67 directly adjacent to its connection with the face 53, the jaw 48 presses flat against the face 56 of the jaw 47 under conditions suitable for allowing relative sliding therebetween in a direction perpendicular to the plane 35 while clamping one of the grip zones 3 and 4 of a testpiece 1 between the faces 52 and 53 of the jaws 47 and 48. The face 67 is otherwise not in contact with the jaw 47 whose face 56 is connected via a step 68 to a rectangular face 69 perpendicular to the planes 34 and 35 and thus set back from the face 56, which face 69 defines the portion 54 of the jaw 47 opposite from the end flange 45 of the arm 31 in a direction defined by the intersection 36 between the planes 34 and 35 and remote from the portion 55 of the jaw 47 about the plane 35. On going away from the plane 35, the face 69 is connected to a plane rectangular face 70 which defines the portion 54 going away from the plane 35 and opposite from the face 62, in a position that is symmetrical to the position of said face 62 about the plane 35 such that the face 70 lies in the same plane as the face 66 of the jaw 47 when the jaw is clamping against a grip zone 3 or 4 of a testpiece 1.

In order to make such clamping possible, the portion 55 of the jaw 47 and the jaw 48 are pierced by through holes 73 and 74 on respective axes 71 and 72 perpendicular to the plane 35 and distributed respectively relative to the face 52 and relative to the face 53 in the same manner as the axes 10 and 11 relative to the main faces 8 of the testpiece 1, respectively in the zone 57 of the grip zone 3 or the grip zone 4, which holes 73 and 74 thus lie on common axes when the two jaws 47 and 48 are placed so as to clamp onto one of the grip zones 3, 4 of a testpiece 1, and they are also disposed on the same axes either as the holes 12 in a grip zone 3 or the holes 13 in a grip zone 4 so as to receive on those axes (not shown) bolts for clamping the two jaws 47 and 48 together perpendicularly to the plane 35 onto the grip zone 3 or the grip zone 4 such that once clamped between the faces 52 and 53 of the two jaws 47 and 48 the grip zone acts as part of a single solid unit including the jaws.

Once each testpiece 1 has been clamped via both grip zones 3 and 4 respectively between the two jaws 47 and 48 of the two clamps 33 or between the two jaws 49 and 50 of the two clamps 32, only the bending zone 2 remains free, in particular to bend, between the two respective clamps 33 or 32, during alternating turning of the arms 31 or 30 about the axes 26 away from a rest position that corresponds to a rest state for both of the testpieces 1, thereby opposing resistance to such alternation bending about the rest state.

With reference to the rest position of the apparatus 19 and to the corresponding rest state of the two testpieces 1, and also with reference to the embodiment described respectively with reference to FIGS. 6 to 18 and with reference to FIGS. 1 and 2, the clamps 33 are placed facing each other as are the clamps 32 via the chamfers of their jaws 47, 48, 49, and 50 and via their slots 46 and 51 in a relative position in which the mean plane 35 of the arms 31 and of the clamps 33 coincide with the mean planes 5 of the corresponding testpieces 1, and similarly their mean planes 34 coincide with the mean planes 6 of said testpieces, with the arms 31 and their clamps 33 being respectively mutually symmetrical about a plane 108 perpendicular to the planes 34 and 35 and coinciding with the mean plane 7 of the corresponding testpiece and with identical relationships existing between the arms 30 and their clamps 32 and the corresponding testpiece 1. In addition, the mean planes 5 of the two testpieces 1 are mutually parallel, mutually symmetrical about the point or center of symmetry 22 on either side of which they are placed, and the mean planes 3 of the two testpieces 1 coincide and contain the point or center of symmetry 22, as do their mean planes 7.

In order to measure the resistance of the bending zones 2 in the two testpieces 1 against alternating bending and as the test progresses, measurements are performed in the preferred embodiment of the invention shown on at least one of the arms 30 and 31, namely on only one of the arms, e.g. an arm 31, in practice, where using one arm has been validated in testing, in order to determine the moment opposing turning of the arm about the corresponding axis 26 by measuring the bending stresses to which the arm 31 is subjected about the plane 35 or about planes parallel to said plane 35.

In order to emphasize these bending stresses, the arm 31 in question, and indeed the other arm 32 and the two arms 30 for reasons of symmetry about the point or center of symmetry 22, present at least one respective zone 75 or 76 that is weak in bending in the plane 35 and in planes parallel thereto, i.e. in a direction that is circumferential relative to the corresponding axis 26, while not contributing to weakness in bending about other directions. Nevertheless, the arms 30 and 31 are intrinsically rigid, e.g. being made of aluminum, it being understood that they ought not to bend during testing, and bending should remain restricted to the bending zones 2 in the two testpieces 1.

In the example shown in FIGS. 9, 12 to 14, and 18, each arm 31 thus presents two zones 75 of weakness in bending, which zones are identical and identically distributed in a direction defined by the mean fiber or intersection 36 between the two planes 34 and 35, and like zones 76 are distributed over the arms 31 in identical manner, from one arm 30 to the other arm 30 and from an arm 30 to an arm 31, in the direction of the mean fibers of said arms. Nevertheless, as shown in FIGS. 10 and 15, it is also possible for each arm 30, 31 to present only one such zone 75, 76 of weakness in bending, disposed identically relative to the mean fiber of the arm, both concerning the zones 75 of the arm 31 and the zones 76 of the arm 30.

Naturally, on each arm 30 and 31, the or each zone 76, 75 of weakness in bending is disposed between the end zone such as 39 for secure connection with the corresponding shaft such as 28, and the end zone such as 40 forming a flange such as 45 for secure connection to a respective one of the jaws 49 or 47 of a respective clamp 32 or 33.

Only one zone 75 is described herein, it being understood that the zones 75 are identical to one another and also that the zones 76 are identical to the zones 75.

In this respect, reference is made to FIG. 14 which shows that in the or each zone 75, the arm 31 is hollowed out in its faces 38 by a pair of notches 77 each of which is defined by a face 78 that is concave, forming a half-circular cylinder about an axis 79 perpendicular to the plane 35 and lying in the same plane as the corresponding face 38, with the face 78 being connected by the face 38 to both of the end zones 39 and 40 of the arms 31, and also being connected to each of its faces 37 on going away from either side of the plane 35.

The axes 79 of the pair of notches 77 together constituting a zone 75 lie in the same plane 80 perpendicular to the two planes 34 and 35, i.e. also perpendicular to the mean fiber of the arm 31 as defined by the intersection 36 of these two planes 34 and 35, and each of the faces 78 presents, relative to its axis 79, a radius $\underline{r}$ that is less than half the dimension D that each face 37 presents perpendicularly to the plane 34, so as to leave a strip 81 of the material constituting the arms 31 between the pair of notches 77, said strip presenting dimensions that are sufficient to ensure that the arm remains rigid during bending tests while nevertheless being more sensitive than the remainder of the arm 31 to the bending stresses that appear during testing.

For this purpose, four strain gauges are used, two of which are placed on one side of the plane 34 and the other two on the other side thereof, in positions that are mutually symmetrical about the plane 34; it is thus possible to place four strain gauges in one of the zones 75 or in the single zone 75 on the plane 80 of said zone 75, with two of the strain gauges being stuck to one of the corresponding faces 78 respectively on either side of the plane 35 in positions that are mutually symmetrical thereabout, and the other two against the corresponding other face 78, likewise respectively on either side of the plane 35 and in positions that are mutually symmetrical thereabout. If at least two zones 75 are provided in the same arm 31, it is also possible to stick such strain gauges on a respective face 78 in respective positions on either side of the plane 35 so as to have two strain gauges in said other one of the zones 75 and the other two strain gauges in said one of the zones 75. In all cases, the strain gauges are placed on the plane 80 of the zone 75 or the corresponding zone 75, i.e. they are placed where the strip 81 is at its narrowest on being measured perpendicularly to the plane 34.

Strain gauges placed in those two manners are shown respectively at 82 and at 83 on the right and on the left of FIG. 9, for the case in which each arm 31 has two zones 75 of weakness in bending, whereas FIG. 10 shows the positioning of two strain gauges 82 respectively on either side of the strip of material 81 of an arm 31 that presents only one zone 75 of weakness in bending.

As shown in FIG. 11, the four strain gauges 82 or 83 are interconnected in a manner that is easily devised by the person skilled in the art so as to constitute a strain gauge bridge 84 which, after prior calibration, delivers a voltage U at all times to an acquisition card 85 of a computer 86, which voltage U is proportional to the moment M of the bending couple to which the arm 31 is subjected due to the reaction from the bending zone 2 of the corresponding testpiece 1 opposing bending, during the alternating relative turning of the arms 30 and 31 and the opposing alternating bending of the bending zone 2 of the two testpieces 1.

In addition, it is also possible to stick a respective strain gauge 87 on each of the main faces 8 of each of the testpieces 1 in its bending zone 2 on the corresponding mean plane 35 perpendicular to the axes 27. The strain gauges 87 measure deformation locally in the bending zones 2 on the surfaces thereof, and they can also be connected via terminals secured to the zone 58 of the corresponding testpiece 1 to a strain gauge bridge enabling the surface deformations of the two testpieces 1 to be measured continuously, thus enabling the computer 86 to record not only the measured moment of the couple as delivered at all times by the bending zone of the testpieces 1 in opposition to the bending, but also to measure the surface deformations of said bending zones 2.

The computer 86 controls the stepper motors of the two motor assemblies 21 in synchronous manner by delivering setpoints to a card 88 for controlling the motors, so as to cause their respective shafts 27 and 28 to turn through a desired angle about the respective axes 26 relative to each other, with the control card 88 returning to the computer 86 the instantaneous value of the angular setpoint delivered to the two motor assemblies 21.

Preparing the necessary programs forms part of the normal skills of a person skilled in the art.

Such a person skilled in the art will readily understand that the method and the apparatus as described above can be used not only to obviate the friction forces that are inherent to the methods and apparatuses of the prior art, but can also be used to perform pure bending tests on two testpieces 1, i.e. bending tests that ensure that the two testpieces are subjected to practically no forces that are normal thereto or that intersect them, thus making it possible to obtain results that are genuinely meaningful in terms of how the bending zone 2 behaves in bending.

Such a method and such apparatus can be applied to testpieces 1 of any shape providing the shape and/or the structure of the testpiece 1 make it possible to ensure that this opposing bending of the two testpieces 1 caused by alternating turning of the arms 30 and 31 of the two motor assemblies 21 preserves the grip zones 3 and 4 of the testpieces 1 stationary in directions perpendicular to the plane 35, i.e. perpendicular to the axes 26, and also stationary in direction relative to said plane 35 so as to ensure that no normal and/or intersecting forces appear in the bending zones 2. Naturally, depending on the shape of the grip zones 3 and 4 of a testpiece 1, the person skilled in the art will adapt the shape of the clamps 32 and 33, i.e. more particularly of the faces such as 52 and 53 which define the slots 46 and 51 for securely receiving the respective grip zones 3 and 4 of a testpiece 1.

Where possible, the clamps should nevertheless have jaws for securely receiving the grip zones 3 and 4 of the two testpieces 1 that remain chamfered in shape, as described above with reference to FIGS. 16 and 17. Two jaws that thus taper towards each other, when seen in the rest position, leave room for a large amount of bending in the bending zone 2, as shown in FIG. 18 where it can be seen that the shape described with reference to FIGS. 16 and 17 makes it possible for each of the grip zones 3 to turn relative to the corresponding grip zone 4 by relative turning of each of the arms 31 relative to the arms 30 of the same motor assembly 21 about the corresponding axis 26 through an angle of up to 90°, with this being performed in alternation in one direction and in the other direction so as to cause each of the bending zones 2 between the two grip zones 3 and 4 of a given testpiece 1 to bend through an angle that can thus be as great as 90°, in each of the two directions, away from the rest state, assuming that the testpiece 1 in the rest state is in the form of a plate having a mean plane of symmetry 6 about which its bending zone 2 can be subjected to bending of the same amplitude in either direction.

Nevertheless, the implementations of the method of the invention and the embodiments of the apparatus of the invention as described above are not the only way of obtaining the possibility that is characteristic of the present invention of causing two mutually identical testpieces 1 to be subjected to alternating opposing bending operations while at least substantially conserving mutual symmetry about a point or center of symmetry 22, and FIGS. 19 to 24 show a configuration in which, when the two testpieces 1 are in the rest state and the bending test apparatus 20 is in the rest position, the axes 89 about which the grip zones 3 and 4 of each testpiece 1 are caused to turn relative to each other are not mutually parallel and mutually symmetrical about the center of symmetry 22 as described with reference to FIGS. 3 to 18, but coincide, each passing through the center of symmetry 22.

In a manner similar to the axes 26 which are vertical in the embodiment described with reference to FIGS. 3 to 18, given that the motor assemblies 21 are supported by being suspended from a structure 23 by means of flexible ties 29, the axes 89 are vertical because of the chosen method of connection between the apparatus 20 and the support 23, however other orientations are possible in both configurations, in association with other methods of connection with a support 23, and in particular if it is chosen to support the bending test apparatus 18, or 19, or 20 on a cushion of air or a liquid mat, such examples not being limiting in any way.

With reference to FIGS. 19, 20, 21, and 24, which show the apparatus 20 in its rest position, with the testpieces 1 being in the rest state, the apparatus 20 is configured as described below by way of non-limiting example.

Like the apparatuses 18 and 19, the apparatus 20 has two mutually identical motor assemblies 19 advantageously constituted by electric stepper motors each having a rotor 91 guided to turn about a respective axis 89 relative to a stator 92.

In this example, the motor assemblies 90 are superposed vertically one above the other, one of them defining the bottom portion of the apparatus 20 while the other defines the top portion. In order to ensure that controlled turning of each rotor 91 relative to the corresponding stator 92 leads to pure bending of the bending zone 2 in each testpiece 1, the rotor 92 of the bottom motor assembly 90 stands on a bottom portion of the support 23 to which it is rigidly secured, while the stator 92 of the top motor assembly 90 is suspended from a top portion of the support 23 via flexible ties 93 that are as long as possible so that any turning of the stator 92 of the top motor assembly 90 about the axis 89 relative to the support 23 under conditions that become clear from the description below, i.e. through an angle restricted to a few tens of degrees, leads in practice to no significant change in the height of the stator 92, i.e. to practically no change in the relative levels of the two motor assemblies 90.

Like each of the motor assemblies 21, each of the motor assemblies 90 has two outlet shafts on a common axis, however in this case they are disposed on the same side of the motor assembly 90 coaxially about the axis 89, i.e. an outlet shaft 93 secured to the rotor 91 lying on the axis 89 and subdivided into two segments that are spaced apart along said axis, and an outlet shaft 94 secured to the stator 92 and subdivided into two segments that are likewise spaced apart along the axis 89, each being tubular in shape and coaxially surrounding a respective one of the segments of the outlet shaft 93 in a relationship for guiding relative turning about the axis 89 while preventing any other form of relative displacement. The two segments of each of the outlet shafts 93 and 94 are situated on the same side of the point or center of symmetry 22 on either side of which there are disposed the segments of the outlet shafts 93 and 94 corresponding respectively to the two motor assemblies 90, as are the rotors 91 and stators 92 of said two motor assemblies 90.

The two segments of the outlet shaft 93 of a given motor assembly 90, and the two segments of the outlet shaft 94 of the same motor assembly 90 are securely connected together by respective corresponding rigid brackets 95, 96, wherein the bracket 96 interconnecting the two segments of the outlet shaft 94 surrounds the bracket 95 connecting together the two segments of the outlet shaft 93 while lying in the same mean plane 97 which coincides with the mean plane of symmetry 6 of the two testpieces 1 if the apparatus 20 is considered in its rest position and each of the testpieces 1 in the rest state, as shown in FIG. 19, 20, 21, and 24.

More precisely, each of the brackets 95 and 96 is constituted by two rigid respective arms 98 and 99 extending radially relative to the axis 89 and secured to the outlet shaft segments 93 and 94 that they connect together, and a rigid respective straight spacer 100, 101 parallel to the axis 89 and rigidly interconnecting the two corresponding arms 98 and 99. In the rest position shown in FIG. 19, 20, 21, and 24, corresponding to the rest state of the two testpieces 1, the brackets 95 and 96 corresponding to one of the motor assemblies 90 lie in the plane 97 on one side of the axis 89 with the two brackets 95 and 96 of the other motor assembly 90 lying on the opposite side thereof.

Towards the axis 89, each spacer 100 is secured to a corresponding clamp 102 of design that may be identical to that of the clamps 32 and 33 as described with reference to the embodiment shown in FIGS. 3 to 18, and that serves to hold a corresponding one of the grip zones 3, 4 of a corresponding testpiece 1 in releasable manner by clamping respective pairs of jaws together which testpiece 1, when in its rest state with the apparatus 20 being in its rest position, presents its mean plane of symmetry 5 perpendicularly to the axis 89, with its mean plane of symmetry 6 coinciding with the plane 97 and consequently including the axis 89, and with its mean plane of symmetry 3 at 90° relative to the plane 97 likewise including the axis 89.

The other grip zone 3 or 4 of each testpiece 1 is secured under the same conditions to a clamp 103 of the same design and situated in a position diametrically opposite to that of the clamp 102 about the axis 89 when the apparatus 20 is in the rest position, which corresponds to each of the testpieces 1 being in its rest state. The clamp 103 is rigidly secured by means of a straight spacer 104 extending parallel to the axis 89, to the bracket 96 corresponding to the other motor assembly 90. When the apparatus 20 is in the rest position and the two testpieces 1 are in the rest state the spacer 104 is connected by a clamp 103 to a determined one of the testpieces 1 and lies in the plane 97 on the side of the axis 89 that is diametrically opposite to the side on which the spacer 100 is located that is secured via a clamp 102 to the other grip zone of the same testpiece 1.

The two motor assemblies 90 as constituted in this way with the brackets 95, 96, the clamps 102, 103, and the spacers 104 are mutually symmetrical about the point or center of symmetry 22, in particular when the apparatus 20 is in the rest position corresponding to both testpieces 1 being in the rest state, which testpieces are then mutually symmetrical about the point or center of symmetry 22.

If, starting from the rest position, the two outlet shafts 93 are caused to turn in controlled manner through the same angle about the axis 89 relative to the corresponding stator 92, in the same direction if the apparatus 20 is considered as a whole, i.e. in mutually opposite directions if each of the two motor assemblies 90 is considered independently of the direction in which it points within the apparatus 20, the arms 98 of the two motor assemblies 90 become angularly offset relative to the arms 99 of the corresponding motor assembly 90 by the same angle in directions corresponding to the turning directions, but overall the symmetry of the apparatus 20, including the symmetry relating to the two testpieces 1 is conserved relative to the point or center of symmetry 22, and the two testpieces 1 are subjected to opposing bending operations, as shown by way of example in FIGS. 22 and 23 which show respectively the bottom and the top testpieces 1 when bent respectively through a right angle between their respective grip zones 3 and 4. This bending is localized in their respective bending zones 2 insofar as the grip zones 3 and 4 are fully held rigidly in the two clamps in this embodiment as in the embodiment described with reference to FIGS. 3 to 18, so that only the bending zone 2 is free, in particular in bending, therebetween.

During such bending and because of symmetry, each of the mean planes 5 of symmetry is kept symmetrical relative to the axis 89 and the axes 89 continue to coincide, passing substantially through the point 22, with any slight offset that may arise between them being due solely to a slight difference in the behavior of the two testpieces 1, under conditions that nevertheless remain negligible in terms of influence on measurements.

These measurements are taken under the same conditions as for the embodiment described with reference to FIGS. 3 to 18 in that, preferably, the resistance opposed to bending by each of the bending zones 2 is measured by measuring a resistive moment in at least one of the arms 98 and 99, it being understood that the arms 98 are mutually identical as are the arms 99, and advantageously present at least one zone that is weakened in bending, said zones being disposed identically relative to the axis 89 in a manner that is entirely similar to that described above with reference to the embodiment of the invention shown in FIGS. 3 to 18.

This embodiment of the invention is therefore not described in greater detail since reference can be made to the embodiment described with reference to FIGS. 3 to 18 for practical points concerning measurement.

Naturally, the two embodiments of the invention as described above merely constitute two non-limiting examples and numerous variants can be made relative thereto without thereby going beyond the ambit of the invention, as defined in the claims.

What is claimed is:

1. A method of testing in pure bending or alternating bending, the method comprising the following succession of steps:
    a) making or selecting a testpiece having two mutually opposite end grip zones and a bending zone interconnecting the two grip zones the testpiece presenting, in a rest state, a first mean plane crossing the bending zone and each of the grip zones and constituting a first plane of symmetry at least for the bending zone, and a mean surface for the bending zone and each of the grip zones, wherein the mean surface is perpendicular to the first mean plane;
    b) leaving the testpiece in the rest state rigidly securing its two grip zones so as to define for each of them a respective pivot axis perpendicular to the first mean plane and occupying a determined first position relative to the respective grip zones and a second position relative to the mean surface; and
    c) imparting controlled opposing turning movements to the two grip zones of the testpiece, optionally in alternation, about the respective pivot axes and away from the rest state, while leaving the pivot axes free to move towards each other or apart from each other, so as to impart optionally alternating bending to the bending zone and so as to study the behavior of the bending zone in pure bending; wherein
    the method is simultaneously performed on two mutually identical testpieces (1) by implementing
    step b) in such a manner that the first mean planes of the two testpieces are mutually parallel and the mean surfaces of the two testpieces are mutually symmetrical about a point when the two testpieces are in the rest state, and in such a manner that the pivot axes of the two testpieces are common and mutually symmetrical about the point; and by implementing
    step c) in such a manner that optionally alternating opposing torques in controlled manner are applied about each pivot axis to the respective corresponding grip zones so as to impose optionally alternating opposing bending movements to the bending zones of the two testpieces, while allowing the pivot axes to move freely relative to each other.

2. A method according to claim 1, the testpiece presenting as its mean surface in its rest state, a second mean plane constituting a second plane of symmetry at least for the bending zone, the method being characterized in that step b) is implemented in such a manner that the second mean planes of the two testpieces coincide when the two testpieces are in the rest state and the pivot axes are placed in the second mean planes, which thus coincide.

3. A method according to claim 1, the testpiece presenting in its rest state a third mean plane which is perpendicular to the first mean plane which is crossed by the bending zone with the grip zones being disposed on respective opposite sides thereof, and constitutes a third plane of symmetry, at least for the bending zone, the method being characterized in that step b) is implemented in such a manner that the third mean planes of the two testpieces coincide and the pivot axes are mutually symmetrical about the third mean planes which thus coincide.

4. A method according to claim 1, wherein during step c), the behavior of the bending zone of the testpieces in pure bending is studied by measuring the resistance opposed to the turning by at least one of the grip zones, in particular to deduce therefrom changes in the resistance to bending of the bending zone.

5. A method according to claim 1 wherein step b) is implemented by connecting each of the grip zones to the corresponding respective pivot axis by plurality of arms, the plurality of arms corresponding to the grip zones of the two testpieces being mutually symmetrical about the point, and by connecting the plurality of arms corresponding to a given pivot axis using respective controlled motors suitable for imparting optionally alternating opposing turning movements to the plurality of arms about the corresponding pivot axis, the controlled motors corresponding to the two pivot axes being mutually identical and being allowed to move freely relative to each other.

6. A method according to claim 5 wherein step b) is further implemented by causing each arm of the plurality of arms to be elastically flexible in the first mean plane of the corresponding testpiece with stiffness that is greater than the stiffness of the bending zone of the testpiece, while otherwise being rigid, and wherein during step c) the resistance opposed to turning is measured by measuring the bending stresses to which at least one of the plurality of arms is subjected in the first mean plane of the corresponding testpiece.

7. A method according to claim 5, wherein the plurality of arms and the controlled motors are arranged in such a manner that during step b) the pivot axes are mutually parallel and disposed respectively on either side of the point.

8. A method according to claim 7, wherein the third mean plane of the testpiece comprises a mutual plane of symmetry for the grip zones of the testpiece, and wherein the plurality of arms which correspond to the grip zones of the two testpieces are mutually identical.

9. A method according to claim 5, wherein the plurality of arms and the controlled motors are arranged in such a manner that during step b), the pivot axes coincide and pass through the point.

10. A method according to claim 1, wherein during step a) each testpiece is made or selected in such a manner as to be in the form of a plate of thickness (e) extending perpendicular to the mean surface.

11. A method according to claim 10, wherein during step a) each testpiece is made or selected in such a manner that the thickness (e) is also constant, at least in the bending zone.

12. A method according to claim 10, wherein during step a), each testpiece is made or selected in such a manner that it presents a dimension ($L_1$) perpendicular to the first mean plane that is constant, at least in the bending zone.

13. A method according to claim 10, wherein during step a) each testpiece is made or selected in such a manner as to present a respective transition perpendicular to the first mean plane between the bending zone and each of the grip zones.

14. Test apparatus for testing a testpiece in pure bending or alternating bending, the testpiece comprising two mutually opposite end grip zones and a bending zone interconnecting the two grip zones the testpiece presenting, in a rest state, a first mean plane crossing the bending zone and each of the grip zones, and constituting a first plane of symmetry at least for the bending zone, and a mean surface for the bending zone and for each of the grip zones, wherein the mean surface is perpendicular to the first mean plane, the apparatus comprising:

a pair of clamps each defining a slot for securely gripping a respective grip zone of the testpiece, the slots presenting, in a relative rest position corresponding to the testpiece being in the rest state, a first mean plane which crosses each of the slots, and a mean surface for each of the slots wherein each slot presents on either side of the mean surface a respective clamping face for clamping the corresponding grip zone of the testpiece and with the mean surface extending perpendicular to the first mean plane of the slots;

means for defining a respective pivot axis for each clamp in such a manner that in the relative rest position of the clamps, the pivot axes are perpendicular to the first mean planes of the slots, and occupy determined positions relative to the corresponding clamps and are free to move towards each other or apart from each other;

controlled means for imparting opposing, optionally alternating turning movements to the clamps about the corresponding pivot axes away from the relative rest position of the clamps, while leaving the pivot axes free to move towards each other or apart from each other; and means for measuring the behavior of the bending zone of the testpiece in pure bending; wherein, the apparatus implements the method according to claim 1 by including:

two mutually identical sets of the pair of clamps, the two sets of the clamps having the first mean planes of their slots mutually parallel and having the mean surfaces of the slots mutually symmetrical about a point when the two sets are occupying respective rest position, in which the two sets are suitable for receiving a respective testpiece in the rest position with the two testpieces being in a relative position such that they are mutually symmetrical about the point;

the means for defining the pivot axes of the pair of clamps are arranged so that the pivot axes are common to the two sets, being mutually symmetrical about the point when the two sets are in their rest positions, and being free to move relative to each other; and the controlled means for imposing opposing and optionally alternating turning movements on the clamps of the two sets comprising controlled motor means for applying opposing, optionally alternating torques about each pivot axis to the corresponding clamps.

15. Apparatus according to claim 14, wherein each testpiece presents as its mean surface in its rest state, a second mean plane constituting a second mean plane of symmetry at least for the bending zone, the slots of pair of clamps possessing as mean surface respective second mean planes between the clamping faces of each clamp when in the rest position, the apparatus being characterized in that the second mean planes of the two sets of the pair are mutually symmetrical about the point when the two sets are in the rest position.

16. Apparatus according to claim 15, wherein each testpiece in its rest state presents a third mean plane that is perpendicular to the first mean plane, that is crossed by the bending zone when the grip zones are disposed respectively on either side thereof, and that constitutes a third plane of symmetry at least for the bending zone, and the slots of the pair of clamps present, in the rest position, a third mean plane on either side of which they are disposed and which is perpendicular to their first mean plane, the apparatus being characterized in that the third mean planes of the two sets of the pair are mutually symmetrical about the point when the two sets are in the rest position.

17. Apparatus according to claim 14, wherein the means for measuring the behavior of the bending zone of the testpieces in pure bending comprise:

means for measuring the resistance opposed to the alternating turning movements by at least one of the clamps; and, where appropriate means for deducing therefrom how the resistance of the testpiece to bending between the clamps changes.

18. Apparatus according to claim 14, wherein
the means for defining the pivot axes of the two sets comprises:
on each of the pivot axes, two respective shafts on the same axis and mounted to turn relative to each other about the corresponding pivot axis; and
at least four arms that are mutually symmetrical about the point, each connecting a respective one of the shafts to a respective one of the clamps corresponding to the same pivot axis; and
the controlled motor means for applying opposing, optionally alternating torques about each pivot axis to the corresponding clamp comprise two mutually identical controlled motors arranged in such a manner as to be capable of moving freely relative to each other, each of the motors being associated with a respective one of the pivot axes and being suitable for imparting opposing, optionally alternating, turning movements to the two respective corresponding shafts.

19. Apparatus according to claim 18, wherein the motors are electric stepper motors.

20. Apparatus according to claim 18, wherein each arm of the plurality of arms is elastically flexible in the first mean plane of the slot of the corresponding clamp with stiffness greater than the stiffness of the bending zone of the corresponding testpiece, and is otherwise rigid, and in that the measurement means comprise means for measuring the bending stresses to which at least one of the plurality of arms is subjected in the first mean plane of the slot of the corresponding clamp.

21. Apparatus according to claim 20, wherein the plurality of arms present in mutually symmetrical positions about the point at least one respective zone that is weakened in bending in the first mean plane of the slot of the corresponding clamp, and wherein
the means for measuring bending stresses are located in the zone of at least one of the plurality of arms.

22. Apparatus according to claim 18, wherein the plurality of arms, the shafts, and the motors are arranged in such a manner that in the rest position the pivot axes are mutually parallel and disposed respectively on either side of the point.

23. Apparatus according to claim 22, wherein the plurality of arms of the apparatus are mutually identical and each testpiece presents as its mean surface in its rest state a second mean plane and a third mean plane,
the second mean plane comprising a second mean plane of symmetry at least for the bending zone, the slots of the pair of clamps possessing as mean surface respective second mean planes between the clamping faces of each clamp when in the rest position, and wherein the second mean planes of the two sets of the pair are mutually symmetrical about the point when the two sets are in the rest position, and
the third mean plane of each testpiece comprising a plane of mutual symmetry for the grip zones and being perpendicular to the first mean plane, that is crossed by the bending zone when the grip zones are disposed respectively on either side thereof, and that comprises a third plane of symmetry at least for the bending zone, and the slots of the pair of clamps present, in the rest position, a third mean plane on either side of which they are disposed and which is perpendicular to their first mean plane, and wherein the third mean planes of the two sets of the pair of clamps are mutually symmetrical about the point when the two sets are in the rest position.

24. Apparatus according to claim 18, wherein some of plurality of the arms, the shafts, and the motors are arranged in such a manner that, in the rest position, the pivot axes coincide and pass through the point.

25. Apparatus according to claim 14, wherein the clamps are chamfered so as to taper towards each other when the clamps are in the rest position.

26. A testing machine for performing testing in pure bending, optionally in alternating bending, for implementing the method according to claim 1, wherein the machine comprises:
two mutually identical motor assemblies that are mechanically mutually independent, each of the identical motor assemblies further comprising:
two clamps each of which is suitable for securely receiving a respective grip zone of a corresponding testpiece;
means for defining a relative pivot axis for the two clamps and occupying a determined position relative to each of the two clamps while in a relative rest position; and
controlled motor means for imparting relative and optionally alternating turning movements to the clamps about the relative pivot axis away from the relative rest position; and
common means for controlling the motor means of the two motor assemblies to impart relative, optionally alternating turning movements to the respective clamps about the respective relative pivot axes.

27. A machine according to claim 26, characterized in that it comprises:
means for measuring the resistance to relative turning opposed by at least one of the clamps.

28. A machine according to claim 26, wherein for each of the motor assemblies respectively,
the means for defining the relative pivot axes of the two clamps comprises:
two shafts mounted on the same axis to turn relative to each other about the relative pivot axis; and
two arms, each of which secures one of the clamps to a respective one of the shafts; and
the controlled motor means for imparting relative, optionally alternating turning movement to the clamps about the relative pivot axes, comprise a controlled motor that is mechanically independent of the control motor of the other motor assembly and that is suitable for imparting relative, optionally alternating, turning movements to the two shafts.

29. A machine according to claim 28, wherein each controlled motor is an electric stepper motor.

30. A machine according to claim 28, wherein
each of the plurality of arms is elastically flexible in a mean plane perpendicular to the pivot axis and is otherwise rigid, and the measurement means comprise means for measuring the bending stresses to which at least one of the plurality of arms is subjected in the mean plane.

31. A machine according to claim 30, wherein each of the plurality of arms presents at least one zone that is weak in bending in the mean plane, and wherein the means for measuring bending stresses are located in the zone of at least one of the arms.

32. A machine according to claim 26, wherein the plurality of arms are mutually identical.

33. A machine according to claims 26, wherein the clamps are chamfered.

* * * * *

UNITED STATES PATENT AND TRADEMARK OFFICE
CERTIFICATE OF CORRECTION

PATENT NO.         : 7,017,423 B2
APPLICATION NO. : 10/524474
DATED                : March 28, 2006
INVENTOR(S)      : Sylvain Calloch et al.

It is certified that error appears in the above-identified patent and that said Letters Patent is hereby corrected as shown below:

Col. 1, line 14, delete "This application is a 371 of PCT/FR03/02515."
Col. 2, line 33, "shafts" should read --shaft--.
Col. 7, line 22, "applies for example" should read --applies, for example,--.
Col. 7, line 25, "implemented-in" should read --implemented in--.
Col. 7, line 30, "apparatus-of" should read --apparatus of--.
Col. 8, line 30, "axes, comprise" should read --axes comprise--.
Col. 15, line 62, "points" should read --point--.
Col. 15, line 62, "is secured" should read --are secured--.
Col. 17, line 25, "are identical" should read --is identical--.
Col. 19, line 3, "jaw 48 shown" shown read --jaw 48, shown--.
Col. 24, line 34, "testpieces 1 in" should read --testpieces 1 is in--.
Col. 25, line 27, "testpieces 1 is" should read --testpieces 1, is--.
Col. 26, line 7, "zones the" should read --zones, the--.
Col. 26, line 29, delete "(1)".
Col. 27, line 3, "by plurality" should read --by a plurality--.
Col. 27, line 53, "zones the" should read --zones, the--.
Col. 28, line 23, "position" should read --positions--.
Col. 28, line 41, "of pair" should read --of the pair--.
Col. 30, line 1, "some of plurality" should read --some of the plurality--.
Col. 30, line 64, "claim" should read --claims--.

Signed and Sealed this

Twenty-ninth Day of August, 2006

JON W. DUDAS
*Director of the United States Patent and Trademark Office*